US006576106B1

(12) United States Patent
Nakazato

(10) Patent No.: US 6,576,106 B1
(45) Date of Patent: Jun. 10, 2003

(54) METHOD FOR SEPARATING AND ASSAYING LIPOPROTEIN, AN ASSEMBLY FOR PERFORMING SUCH A METHOD, AND A SYSTEM INCLUDING SUCH AN ASSEMBLY

(75) Inventor: Tokiya Nakazato, Urawa (JP)

(73) Assignee: Helena Laboratories Co., Ltd., Saitama (JP)

(*) Notice: Subject to any disclaimer, the term of this patent is extended or adjusted under 35 U.S.C. 154(b) by 0 days.

(21) Appl. No.: 09/549,925

(22) Filed: Apr. 14, 2000

(30) Foreign Application Priority Data

Apr. 14, 1999 (JP) .............................. 11-107258
Apr. 7, 2000 (JP) ....................... 2000-107103

(51) Int. Cl.[7] .................. B01D 57/02; B01D 59/42; B01D 59/50; B01D 61/42; B01D 61/58; C02F 1/469; C07K 1/26; C08F 2/58
(52) U.S. Cl. .................. 204/461; 204/466; 204/467; 204/456; 204/606; 204/616; 204/618; 356/39; 356/344
(58) Field of Search ................. 204/466, 467, 204/456, 461, 606, 616, 618; 356/39, 344

(56) References Cited

U.S. PATENT DOCUMENTS

| 4,420,383 A | * | 12/1983 | Fujiwara et al. | ............ 204/457 |
| 4,909,920 A | | 3/1990 | Sarrine et al. | |
| 4,920,498 A | * | 4/1990 | Kaneko | ...................... 204/546 |
| 5,068,019 A | * | 11/1991 | Yoshida et al. | ............. 204/456 |
| 5,316,908 A | * | 5/1994 | Carlson et al. | ............. 204/461 |
| 5,795,455 A | * | 8/1998 | Pannetier | ..................... 204/458 |
| 5,905,143 A | * | 5/1999 | Johnson et al. | ............. 210/660 |

FOREIGN PATENT DOCUMENTS

EP    0 806 659    11/1997

OTHER PUBLICATIONS

Voet and Voet, Biochemistry, Section 5–4, pp. 94–100, 102, 104, 105, 292.*
LDL (www.sigmaaldrich.com)—product search No. L5402.*
Lynch et al., "Routine Lipid Screening By Cholesterol Staining Electrophoresis–Including Lipoprotein (a) Cholesterol (Lp(a)–c)" Australian Journal Of Medical Science, vol. 19:123–126, (1998).
Russell et al., "Electrophoretic quantitation of LDL–Cholesterol Using The Helena REP", Clinical Chemistry, vol. 39(6):1122, (1993) XP001021081.
"Charge properties of low density lipoprotein subclasses" LaBelle et al., Journal of Lipid Research, vol. 38, 1997, pp. 690–700.*
"Quantitative measurement of lipoprotein surface charge by agarose gel electrophoresis" Sparks et al., Journal of Lipid Research, vol. 33, 1992, pp. 123–130.*

* cited by examiner

Primary Examiner—Jill Warden
Assistant Examiner—Jennine Brown
(74) Attorney, Agent, or Firm—Venable, LLP; Robert J. Frank; Nancy J. Axelrod

(57) ABSTRACT

A method for separating and assaying lipoprotain to determine a degree of modification of a predetermined component in a specimen of lipoprotein, comprising the step of: determining a distance "a" from an application point of the standard sample to a fraction corresponding to the predetermined lipoprotein using an electrophoretic pattern obtained by electrophoresis of a standard sample; determining a distance "b" from the application point of the specimen to a fraction corresponding to the predetermined lipoprotein using electrophoretic pattern obtained by electrophoresis of a specimen; comparing the distance "a" and the distance "b" to determine a relative mobility "z(=b/a)" of the specimen to the standard sample, wherein the degree of modification of the predetermined component in the specimen being judged on the basis of the relative mobility "z".

36 Claims, 12 Drawing Sheets

| INPUT OF CONTROL VALUE | | |
|---|---|---|
| RELATIVE MOBILITY | 1.125 | ~701 |
| DISTANCE OF LDL | 64 | ~702 |

REGISTRATION 703

CANCEL

FIG. 7

METHOD FOR SEPARATING AND ASSAYING LIPOPROTEIN, AN ASSEMBLY FOR PERFORMING SUCH A METHOD, AND A SYSTEM INCLUDING SUCH AN ASSEMBLY

This application is based on Patent Application Nos. 11-107258 (1999) filed on Apr. 14, 1999 in Japan and 2000-107103 (2000) filed on Apr. 7, 2000, the content of which is incorporated hereunto by reference.

BACKGROUND OF THE INVENTION

1. Field of the Invention

The present invention relates to separation and assay of lipids in a sample such as serum or plasma in the field of medical research, biological research and the like. More specifically, the present invention relates to a method for separating and assaying lipoproteins contained in serum or plasma by means of electrophoresis; an assembly for performing such a method; and a system including such an assembly for separating and assaying lipoproteins, using electrophoresis to estimate the modific ation of lipoprotein by detecting quantitative and qualitative abnormalities of apoprotein in the lipoprotein.

2. Description of the Related Art

Lipoprotein in serum or plasma is a complex of lipid and protein, which includes cholesterol, phospholipid, and neutral fat. Therefore, an abnormality of lipoprotein reflects an abnormality of lipid metabolism, which can be estimated by a process including the steps of separating lipoproteins contained in serum or plasma and performing quantitative and qualitative analyses of the lipoprotein fraction with respect to any abnormalities thereof. Such a method for separating and assaying lipoprotein is one of the important clinical tests for the diagnosis and treatment of a disease affecting lipid metabolism such as hyperlipemia, coronary arteriosclerosis, hypothyroidism, obstructive liver disease, diabetes mellitus, and renal insufficiency.

As an approach to fractionating lipoproteins in a sample, there have been known methods using ultracentrifugal and electrophoretic techniques. The electrophoresis method uses an agarose film, a cellulose-acetate film, or a polyacrylamide gel(PAG) as a plate.

In the ultracentrifugal separation method, lipoproteins in serum can be separated from each other with respect to their respective specific gravities. The resulting fractions are generally referred as: High Density Lipoprotein (HDL); Low Density Lipoprotein(LDL); Very low Density Lipoprotein(VDL); and Chylomicron(CM), respectively.

Regarding the ultracentrifugal separation method, however, it takes much time to prepare a sample to be subjected to an ultracentrifugal machine and to fractionate such a sample. In addition, even finer fractionation of the sample is necessary for finer and detailed separation of lipoproteins to understand conditions during the separation. For this reason, it is difficult to perform the method of separating and assaying lipoprotein by means of ultracentrifugation in a clinical examination as a routine way to detect any abnormality in the target fraction or characterize the results of the separation for a specific disease.

In the electrophoretic separation method, on the other hand, lipoproteins in the solution can be fractionated mainly with respect to differences in their electrophoretic mobilities. In this case, the conditions of lipoprotein separation can be understood visually. For this reason, electrophoretic separation is often used in routine examination for separating and assaying lipoproteins in a sample. It is noted that the results of both electrophoretic and ultracentrigual procedures for separating lipoproteins show good correlation with each other. When a lipoprotein is fractionated using the electrophoretic technique, lipoprotein is separated into the fractions of $\alpha$(HDL), pre $\beta$(VLDL), $\beta$(LDL), and the point of origin(cylomicron). These fractions correspond to lipid species visualized by a lipid stain such as fat red 7B for estimating the amount of lipid in each fraction. For the convenience of one of skill in the art, the name of each lipoprotein fraction obtained by the prior art ultracentrifugal separation is described in the parentheses attached to each fraction name of the above electrophoresis.

The fundamental structure of lipoprotein is composed of a core part formed of a neutral fat(triglyceride) and cholesterol ester, a single hydrophilic lipid membrane that covers the core part, and one or more apoproteins adhered to the surface of such a membrane. The type of the apoprotein differs for each fraction of lipoprotein. That is, mainly, apoproteins in HDL are apoprotein A-I, A-II, A-IV, C-I, C-II, C-III, and E. Apoproteins in VLDL are apoprotein C-I, C-II, E, and B-100. Apoprotein in LDL is apoprotein B-100. Apoproteins in chylomicron are apoprotein A-I, A-II, A-IV, C-I, C-II, C-III, E, and B-48. In the electrophoretic process, a difference in the isoelectric point of each apoprotein contained in the lipoprotein is reflected as a difference in mobility of each fraction.

Since arteriosclerosis is a cause of adult diseases such as coronary arteriosclerosis, it is an important problem in basic and clinical medicine to prevent or treat arteriosclerosis. In particular, because of the recent increase in the number of patients exhibiting arteriosclerosis at young ages, and because patients with diabetes are liable to develop arteriosclerosis, management of lipid in serum is required to be stricter. For example, from epidemiological investigations conducted by the Framingham Institute and the like, it has been shown that the serum cholesterol value, especially the cholesterol value of low-density lipoprotein(LDL), is considered to be a most important,factor in atherosclerosis, which is a cause of coronary artery diseases.

The basis of cholesterol in LDL causing arteriosclerosis is that a macrophage is foamed by taking in modified LDL through a particular receptor, and the remnant adheres onto the vascular wall. Therefore, a screening examination of the modified LDL is necessary.

Here, "modified LDL" is a generic name of variously modified LDL such as oxidized LDL, acetyl LDL, saccharized LDL, and MDA-LDL(malondialdehyde LDL). Further, the term "modification" used in the present specification means modification in a broad sense as normally used by one of skill in the art for modification of lipid or protein. For example, for a lipoprotein component contained in a blood sample, it includes not only modification caused by changes in physical or chemical environment in vivo such as a lipid metabolic anomaly in the body but also modification caused by changes in physical or chemical environment in vitro after sampling, which will be obvious to one of ordinary skill in the art without describing practical examples.

In general, it is said that small-dense LDL is liable to be doxidized. Therefore, as a screening examination of modified LDL, several methods have been tried to detect the ratio of small-dense LDL in lipoprotein. For example, there is a method by the electrophoretic process using PAG having a predetermined pore size and a high molecular sieving effect of PAG, first the smallest-particle (the largest mobility) HDL is separated, and then LDL, VLDL, and chylomicron are separated in order. Specifically, in the lipoprotein fractionation by the PAG electrophoretic process, lipoprotein is fractionated according to the difference in sizes of the particles contained in the lipoproteins, rather than by the difference in isoelectric points of particles contained in the lipoproteins.

For detecting the ration of small-dense LDL using the PAG electrophoretic process, there is a method using the relative distance between each fraction with respect to the position of the VLDL fraction. In this method, electrophoresis using a polyacrylamide gel is carried out, where the electrophoretic migration distance from the central position of the VLDL fraction to the central position of the LDL fraction is defined as "x", and the electrophoretic migration distance from the central position of the VLDL fraction to the central position of the HDL fraction is defined as "y"; a relative electophoretic migration distance(Rf value or Rm value) is determined by the ratio(x/y) of these distances. The obtained value is compared with a value obtained for a normal standard sample in which the LDL is not small-dense. Here, the normal value means a value obtained by the same method for lipoprotein in which the LDL is not small-dense.

As described above, an object of the prior art method for separating and assaying lipoprotein by the PAG electrophoretic process is to determine the ratio of small-dense LDL in lipoprotein, wherein a relative migration distance of the LDL fraction is determined with respect to both VLDL and HDL fractions after electrophoresis. The relative migration distance reflects the difference in particle sizes, but does not reflect qualitative anomalies or quantitative anomalies of specific apoproteins each having different types or different numbers of apoproteins. Especially, lipoprotein fractionation utilizing PAG electrophoresis is not preferred for making a comparison between the normal LDL fraction having non-modified apoprotein B-100 and the modified LDL fraction in which the apoprotein B-100 is subject to some modification. On the other hand, an apoprotein in lipoprotein is directly responsible for a lipid metabolism in the body, so that the detection of an abnormality of the apoprotein may be very useful from a clinical standpoint.

SUMMARY OF THE INVENTION

For solving the problems described above and for simply determining a degree of modification of lipoprotein that reflects a quantitative or qualitative abnormality of apoproteins in lipoprotein, especially of modified LDL, based on its different isoelectric point in comparison with a normal one, a first object of the present invention is to provide a method for separating and assaying lipoprotein in a sample such as serum or plasma of human or mammals.

A second object of the present invention is to provide an assembly for performing such a novel method.

A third object of the present invention is to provide a system that includes such an assembly and optionally a computing device for controlling the assembly.

In a first aspect of the invention, there is provided an assembly for separating and assaying lipoprotein to determine a degree of modification of a predetermined component in a specimen using an electrophoretic pattern of a standard sample containing a lipoprotein having the predetermined component and an electrophoretic pattern of the specimen containing a lipoprotein having component of a same kind as the predetermined component, comprising:

an electrophoretic pattern preparation means for performing electrophoresis of the standard sample and the specimen to fractionate lipoprotein of each sample, then staining respective predetermined component using a reagent for detecting the respective predetermined component by staining the respective predetermined component in the respective lipoprotein to prepare respective electrophoretic pattern with visualized the respective predetermined component;

a waveform diagram preparation means for optically scanning the respective electrophoretic pattern with visualized the respective predetermined component and converting the respective electrophoretic pattern into an optical density waveform to prepare respective waveform diagram of the respective predetermined component; and a means for judging the degree of modification of the predetermined component in the specimen by mathematically processing the respective electrophoretic patterns; wherein the means for judging the degree of modification of the predetermined component comprises:

a first means for determining a distance "a" from an application point of the standard sample to a central position of a fraction corresponding to the predetermined component in the standard sample from electrophoretic pattern of the predetermined component of the standard sample;

a second means for determining a distance "b" from an application point of the specimen to a central position of a fraction corresponding to the predetermined component in the specimen from electrophoretic pattern of the predetermined component of the specimen; and a third means for comparing the distance "a" with the distance "b" to determine a relative mobility "z(=b/a)" of the specimen to the standard sample, wherein the degree of modification of the predetermined component in the specimen being judged on the basis of the relative mobility "z".

Here, the degree of modification of the predetermined component may be obtained as the ratio of modification "M" by substituting the relative mobility "z(=b/a)" into an equation of:

$$M=b/a-1=(b-a)/a \tag{1}$$

The degree of modification of the predetermined component may be obtained as a modification frequency "M" by substituting the relative mobility "z(=b/a)" into an equation of:

$$M'=k(b/a-1)=k(b-a)/a \tag{2}$$

wherein "k" is a constant (k>0).

The standard sample may be a standard serum not containing modified lipoprotein and the specimen may be a serum.

The predetermined component may be a low-density lipoprotein.

The predetermined component may be a lipid.

The electrophoresis may be carried out by an electrophoretic apparatus using a plate comprising an agarose gel as a main ingredient.

In a second aspect of the present invention, there is provided an assembly for separating and assaying lipoprotein to determine a degree of modification of a predetermined component in a specimen using an electrophoretic pattern of a standard sample containing a lipoprotein having the predetermined component, an electrophoretic pattern of the specimen containing a lipoprotein having component of a same kind as the predetermined component, and an electrophoretic pattern of an indicator sample containing a marker component capable of being an indicator of the predetermined component, comprising:

an electrophoretic pattern preparation means for performing electrophoresis of the standard sample and the specimen and the indicator sample to fractionate each sample, then staining respective components using reagents for detecting the predetermined component in respective fractions of the standard sample and the specimen, and the marker component in fraction of the indicator sample by staining thereby preparing respective electrophoretic patterns with visualized the respective components;

a waveform diagram preparation means for optically scanning the visualized respective electrophoretic patterns and converting the respective electrophoretic pattern into an optical density waveform to prepare respective waveform diagram of the respective predetermined component and the marker component; and a means for judging the degree of modification of the predetermined component in the specimen by mathematically processing the respective electrophoretic patterns; wherein the means for judging the degree of modification of the predetermined component have first measuring means and second measuring means, for judging the degree of modification of the predetermined component in the specimen based on a relative mobility of the indicator sample determined by the two measuring means, wherein the first measuring means comprising:
  a first means for determining a distance "a" from an application point of the standard sample to a central position of a fraction corresponding to the predetermined component in the standard sample, from the waveform diagram of the standard sample,
  a second means for determining a distance "c" from an application point of the indicator sample to a central position of a fraction corresponding to the marker component in the indicator sample, and
  a third means for comparing the distance "a" with the distance "c" and determining a relative mobility "$z_1(=c/a)$" of the indicator sample to the standard sample, the second measuring means comprising:
  a fourth means for determining from the waveform diagram of the specimen a distance "b" from an application point of the specimen to a central position of a fraction corresponding to the predetermined component in the specimen, from the waveform diagram of the indicator sample a distance "c" from an application point of the indicator sample to a central position of a fraction corresponding to the marker component in the indicator sample, and
  a fifth means for determining a relative mobility "$z_2(=b/a=b \cdot z_1/c)$" of the specimen from the relative mobility "$z_1$" determined by the first measuring means and the distance "b" and the distance "c" determined by the second measuring means.

Here, the degree of modification of the predetermined component may be obtained as the ratio of modification "M" by substituting the relative mobility "$z_2(=b/a=b \cdot z_1/c)$" into an equation of:

$$M = b \cdot z_1/c - 1 \qquad (3)$$

The degree of modification of the predetermined component may be obtained as modification frequency "M'" by substituting the relative mobility "$z_2(=b/a=b \cdot z_1/c)$" into an equation of:

$$M' = k(b \cdot z_1/c - 1) \qquad (4)$$

wherein "k" is a constant (k>0)).

The standard sample may be a standard serum not containing modified lipoprotein, the specimen may be a serum, and the indicator sample may be a serum stored by adding a stabilizer.

The standard sample may be a standard serum not containing modified lipoprotein, the specimen may be a serum, and the indicator sample may contain an alcohol dehydrogenation enzyme capable of being a marker. In the second measuring means, furthermore, the fourth means may be a means for simultaneously determining the distance "b" and the distance "c" by subjecting a mixture of the indicator sample and the specimen to electrophoresis.

The first predetermined component may be low-density lipoprotein.

The first predetermined component may be lipid.

The electrophoresis may be carried out by an electrophoretic apparatus using a plate comprising agarose gel as a main ingredient.

In a third aspect of the present invention, there is provided a method for separating and assaying lipoprotein to determine a degree of modification of a predetermined component in a specimen using an electrophoretic pattern of a standard sample containing a lipoprotein having the predetermined component and an electrophoretic pattern of the specimen containing a lipoprotein having component of a same kind as the predetermined component, comprising:

an electrophoretic pattern preparation step for performing electrophoresis of the standard sample and the specimen to fractionate lipoprotein of each sample, then staining respective predetermined component using a reagent for detecting the respective predetermined component by staining the respective predetermined component in the respective lipoprotein to prepare respective electrophoretic pattern with visualized the respective predetermined component;

a waveform diagram preparation step for optically scanning the respective electrophoretic pattern with the visualized respective predetermined component and converting the respective electrophoretic pattern into an optical density waveform to prepare respective waveform diagram of the respective predetermined component; and a step for judging the degree of modification of the predetermined component in the specimen by mathematically processing the respective electrophoretic patterns; wherein the step for judging the degree of modification of the predetermined component comprising:
  a first step for determining a distance "a" from an application point of the standard sample to a central position of a fraction corresponding to the predetermined component in the standard sample from electrophoretic pattern of the predetermined component of the standard sample;
  a second step for determining a distance "b" from an application point of the specimen to a central position of a fraction corresponding to the predetermined component in the specimen from electrophoretic pattern of the predetermined component of the specimen; and a third step for comparing the distance "a" with the distance "b" to determine a relative mobility "z(=b/a)" of the specimen to the standard sample, wherein the degree of modification of the predetermined component in the specimen being judged on the basis of the relative mobility "z".

Here, the degree of modification of the predetermined component may be obtained as the ratio of modification "M" by substituting the relative mobility "z(=b/a)" into an equation of:

$$M=b/a-1=(b-a)/a \tag{1}$$

The degree of modification of the predetermined component may be obtained as a modification frequency "M'" by substituting the relative mobility "z(=b/a)" into an equation of:

$$M'=k(b/a-1)=k(b-a)/a \tag{2}$$

wherein "k" is a constant (k>0)).

The standard sample may be a standard serum not containing modified lipoprotein and the specimen may be a serum.

The predetermined component may be a low-density lipoprotein.

The predetermined component may be a lipid.

The electrophoresis may be carried out by an electrophoretic apparatus using a plate comprising an agarose gel as a main ingredient.

In a fourth aspect of the invention, there is provided a recording medium storing a programming for performing the above method for separating and assaying lipoprotein.

In a fifth aspect of the invention, there is provided a system for separating and assaying lipoprotein, comprising: a computer for performing programming stored in the above recording medium, and an assembly for separating and assaying lipoprotein operating according to an instruction based on the programming from the computer.

In a sixth aspect of the invention, there is provided a method for separating and assaying lipoprotein to determine a degree of modification of a predetermined component in a specimen using an electrophoretic pattern of a standard sample containing a lipoprotein having the predetermined component, an electrophoretic pattern of the specimen containing a lipoprotein having component of a same kind as the predetermined component, and an electrophoretic pattern of an indicator sample containing a marker component capable of being an indicator of the predetermined component, comprising:

an electrophoretic pattern preparation step for performing electrophoresis of the standard sample and the specimen and the indicator sample to fractionate each sample, then staining respective components using reagents for detecting the predetermined component in respective fractions of the standard sample and the specimen, and the marker component in fraction of the indicator sample by staining thereby preparing respective electrophoretic patterns with visualized the respective components;

a waveform diagram preparation step for optically scanning the visualized respective electrophoretic patterns and converting the respective electrophoretic pattern into an optical density waveform to prepare respective waveform diagram of the respective predetermined component and the marker component; and a step for judging the degree of modification of the predetermined component in the specimen by mathematically processing the respective electrophoretic patterns; wherein the step for judging the degree of modification of the predetermined component has a first measuring step and a second measuring step, for judging the degree of modification of the predetermined component in the specimen based on a relative mobility of the indicator sample determined by the two measuring steps, wherein the first measuring step comprising:
a first step for determining a distance "a" from an application point of the standard sample to a central position of a fraction corresponding to the predetermined component in the standard sample, from the waveform diagram of the standard sample,
a second step for determining a distance "c" from an application point of the indicator sample to a central position of a fraction corresponding to the marker component in the indicator sample, from the waveform diagram of the indicator sample, and
a third step for comparing the distance "a" with the distance "c" and determining a relative mobility "$z_1$(=c/a)" of the indicator sample to the standard sample, the second measuring step comprising:
a fourth step for determining from the waveform diagram of the specimen a distance "b" from an application point of the specimen to a central position of a fraction corresponding to the predetermined component in the specimen,
a fifth step for determining from the waveform diagram of the indicator sample a distance "c" from an application point of the indicator sample to a central position of a fraction corresponding to the marker component in the indicator sample, and
a sixth step for determining a relative mobility "$z_2$(=b/a=b·$z_1$/c)" of the specimen from the relative mobility "$z_1$" determined by the first measuring step and the distance "b" and the distance "c" determined by the second measuring step.

Here, the degree of modification of the predetermined component may be obtained as a ratio of modification "M" by substituting the relative mobility "$z_2$(=b/a=b·$z_1$/c)" into an equation of:

$$M=b·z_1/c-1 \tag{3}$$

The degree of modification of the predetermined component may be obtained as a modification frequency "M'" by substituting the relative mobility "$z_2$(=b/a=b·$z_1$/c)" into an equation of:

$$M'=k(b·z_1/c-1) \tag{4}$$

wherein "k" is a constant (k>0))

The standard sample may be a standard serum not containing modified lipoprotein, the specimen may be a serum, and the indicator sample may be a serum stored by adding a stabilizer.

The standard sample may be a standard serum not containing modified lipoprotein, the specimen may be a serum, and the indicator sample may contain an alcohol dehydrogenation enzyme capable of being a marker. In the second measuring step, furthermore, the fourth step and the fifth step are simultaneously performed by subjecting a mixture of the indicator sample and the specimen to electrophoresis.

The first predetermined component may be a low-density lipoprotein.

The first predetermined component may be a lipid.

The electrophoresis may be carried out by an electrophoretic apparatus using a plate comprising agarose gel as a main ingredient.

In a seventh first aspect of the invention, there is provided a recording medium storing a programming for performing the above method for separating and assaying lipoprotein.

In a eighth aspect of the invention, there is provided a system for separating and assaying lipoprotein, comprising: a computer for performing programming stored in the above recording medium, and an assembly for separating and assaying lipoprotein operating according to an instruction based on the programming from the computer.

When an electrophoretic apparatus of agarose plate is used in the above method for separating and assaying lipoprotein and assembly to be used for performing such a method, thin film of agarose is used for the plate. Alternatively, a thin film comprising a mixture of agarose and agar can also be used (such a plate is hereinafter referred to as agarose gel). This agarose plate in the form of agarose or agarose gel is preferably prepared from a solution using in a concentration range of 0.4%(W/W) to 1.2%(W/W), more preferably 0.5%(WJW) to 0.8%(W/W) to the buffer solution. Further, the applied voltage during electrophoresis is preferably 200 to 500V when an agarose thin film of 120 mm in length, 130 mm in width and 500 μm in film thickness is used. Still further, it is preferable that a plate comprising agarose gel contains bovine serum albumin (BSA) of about 0.01 to 0.5%(W/W).

Instead of using the above agarose gel, an electrophoretic apparatus using a plate based on cellulose acetate, agar and the like or a capillary electrophoretic apparatus can be used.

The above and other objects, effects, features and advantages of the present invention will become more apparent from the following description of the embodiments thereof taken in conjunction with the accompanying drawings.

BRIEF DESCRIPTION OF THE DRAWINGS

FIG. 7 is a schematic diagram showing a CRT screen for inputting marker data, as an example of screen displayed on the CRT provided in a system for separating and assaying lipoprotein according to the present invention;

DETAILED DESCRIPTION OF PREFERRED EMBODIMENTS

Figure 1:
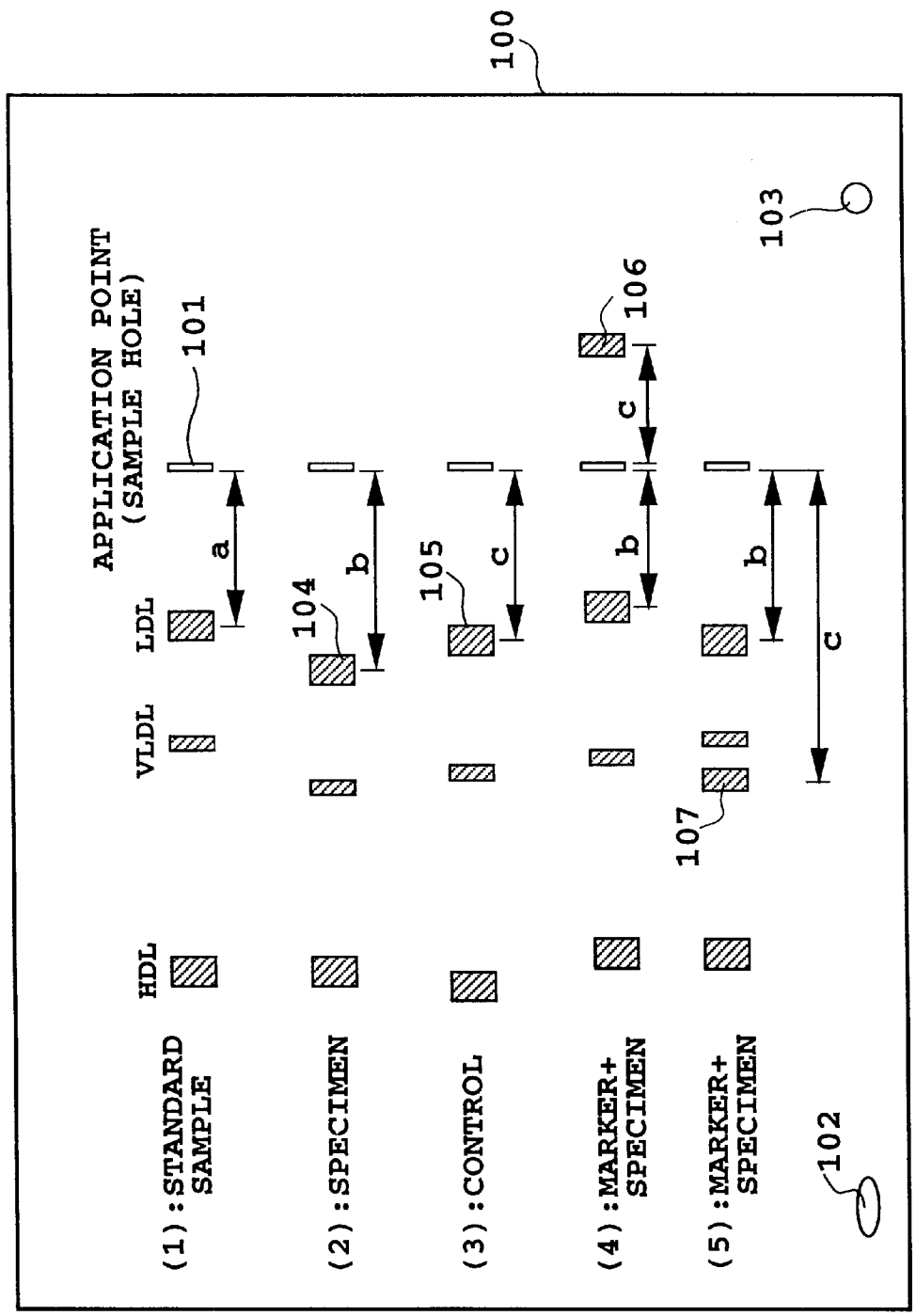
FIG. 1 is a schematic electrophoretic pattern of lipoprotein in serum obtained by an electrophoresis, explaining the principle of the present invention.

The method for separating and assaying lipoprotein according to the present invention uses electrophoresis to determine a degree of modification of lipoprotein, for example, the degree of modification of modified LDL according to a change in isoelectric point caused by quantitative and qualitative anomalies of apoprotein contained in lipoprotein by a simple procedure.

Here, LDL will be mainly described as an example which carries cholesterol synthesized in the liver to other tissues.

LDL is a dangerous factor of arteriosclerosis diseases (myocardiac infarction, stenocardia, brain infarction, and the like), and it is important for treatment of arteriosclerosis diseases to investigate quantitative and qualitative anomalies of LDL. As already described, LDL apoprotein is composed only of B-100, so when the lipid component constituting LDL is modified, the amount of negative charge of apoprotein B-100 changes. Therefore, when a sample containing LDL having modified lipid is subjected to electrophoresis at its isoelectric point, the modified LDL shows a different mobility from that of LDL of a standard sample (it is assumed to be not containing modified lipid). The inventors have accomplished the method for separating and assaying lipoprotein using electrophoresis as will be described below with an eye on a difference between normal LDL and modified LDL.

<Separation and Assay of Lipoprotein Using Electrophoretic Process>

The method for separating and assaying lipoprotein according to the present invention utilizes an electrophoretic process using a plate based on agarose or cellulose acetate as a main ingredient. Here, an electrophoretic process using agarose as a plate is described. Agarose is used as a plate in electrophoresis of nucleic acid and protein because molecules thereof are hydrogen bonded with each other to form a network structure, preparation of a solution is easy, is nontoxic, and extraction operation after electrophoresis is simple.

In the present invention, agarose concentration for enabling separation of lipoprotein is studied, and it is determined that agarose is dissolved and used in a concentration range of 0.5%(W/W) to 1.2%(W/W) in a buffer solution such as tris-barbital, barbital sodium trisin or the like.

When an agarose thin film of 120 mm in length, 130 mm in width, and 500 μm in film thickness is used, applied voltage in electrophoresis is set to about 300 to 500V, 30 to 70 mA. However, the temperature of the agarose plate is required to be constant in a range of generally 10. to 25. during electrophoresis. The temperature distribution on the plate is preferably within ±1., more preferably within ±0.5., because the mobility changes with temperature.

The plate comprising agarose used in the present invention contains the predetermined amount 0.01% to 0.5%, more preferably 0.04% to 0.2% of bovine serum albumin (BSA). This is because if free fatty acid in serum exceeds a predetermined amount, it affects separation rate of HDL, VLDL, LDL and the like, however, by containing BSA in the plate, the separation rate can be prevented from being changed.

Further, as types of electrophoretic apparatus, there are known a horizontal type and a vertical type, and either of these types can be used. However, in the present embodiment use of a horizontal type of electrophoretic apparatus is described. In the present invention, REP of HELENA LABORATORIES CORPORATION (U.S.A.) is used as an electrophoretic apparatus, however, the present invention is not limited to this type.

The principle of the method for separating and assaying lipoprotein according to the present invention will be described with reference to FIG. 1. In the figure, reference numeral 100 indicates an electrophoretic pattern (hereinafter simply referred to as pattern) formed on an agarose plate (also called agarose thin film), 101 is a sample hole formed in the plate (also called an application point), and 102 and 103 are holes utilized when positioning the plate on a densitometer (which will be described later). In FIG. 1, five electrophoretic patterns are obtained by applying five different types of samples into five sample holes 101 and subjecting them to electrophoresis. First, an example of separating and assaying lipid in first and second samples will be described.

The first sample (hereinafter also referred to as standard sample (1)) is a standard serum. That is, it has been sampled from healthy young people not having diseases affecting serum lipoprotein such as cardiovascular diseases, in which it is assumed that modification of LDL is not substantially noted. In FIG. 1, fractions of LDL (low density lipoprotein), VLDL (very low density lipoprotein), and HDL (high density lipoprotein) obtained by electrophoresis of the standard sample (1) are shown. The distance from the application point 101 to the central position of LDL fraction is represented as "a".

The second sample (hereinafter also referred to as specimen (2) is serum which is highly possible to contain modified LDL, sampled from a patient having or suspected to have a disease affecting serum lipoprotein such as cardiovascular diseases. The specimen (2) have potential for modification of LDL. When the specimen (2) is subjected to electrophoresis, fractions of LDL, VLDL, and HDL are obtained as with the first sample. However, mobility of each fraction is different from the standard sample (1). Here, the distance from the application point 101 of the specimen (2) to the central position of a fraction 104 corresponding to LDL (hereinafter simply referred to as LDL fraction) is represented to as "b".

In LDL fraction 104 of the specimen (2), it is considered that when LDL is modified, the negative charge of apoprotein B-100 forming the modified LDL is increased compared with normal LDL of the standard sample (1). Therefore, since the separation rate of modified LDL is faster than the separation rate of normal LDL, resulting in distance "b" >distance "a". For example, therefore, the degree of modification of the LDL contained in the specimen (2) or the degree of modification of the predetermined component contained in the LDL can be estimated by obtaining the relative mobility "z=(b/a)" of the distance "b" to the distance "a" and then making a comparison between the distance "a" and the distance "b". By the way, the term "predetermined component" denotes a specific lipid such as cholesterol or a protein such as apoprotein contained in lipoprotein. Further, the term "degree of modification of predetermined component" denotes a ratio, frequency, classification symbol, percentage, or the like of modification degree of the predetermined component such as LDL or lipid, in addition to a relative mobility itself.

An example of representation of degree of modification will be described. If the LDL contained in the specimen is not modified, the distance "a" equals to the distance "b" and thus the relative mobility "z" takes on "1 (one)". Thus, the ratio of modification "M" of the specimen can be obtained by subtracting "1(one)" from the relative mobility "z". That is, the degree of modification of the specimen can be represented as the ratio of modification "M" by substituting the relative mobility "z" into an equation of:

$$M = b/a - 1 = (b-a)/a \tag{1}$$

According to the equation (1), the relative mobility "z" takes on "1(one)" if the specimen is not modified and then the ratio of modification "M" of the specimen takes on "0(zero)". If the ratio of modification "M" takes on the value larger than zero (i.e., M>0), it is determined that the LDL is a modified one. If the ratio of modification "M" takes on the value smaller than zero (i.e., M<0), we judge that the LDL is a modified one with an abnormality of its component. If the ratio of modification "M" takes on a negative value, in general, it is suspected that there is a hepatic or biliary tract disease and the like.

The modification frequency "M'" of lipoprotein can be represented as an integer by the, following equation (2) in which the constant "k" (k>0) can be appropriately and selectively from any values.

$$M' = k(b/a - 1) = k(b-a)/a \tag{2}$$

The modification frequency "M'" can be also represented as a classification symbol such as "large", "medium", and "small". For another representation, the modification frequency of LDL can be also represented as a ratio of the distance "a" from an application point of the standard sample when the modification frequency "M'" is represented as a percentage of "a/a+b".

Further, when data on the relative mobility and the degree of modification of the sample containing modified LDL corresponding to respective diseases and the standard sample(1) are accumulated by different hepatic and biliary tract diseases in the memory of a computer which will be described later, a disease corresponding to the specimen(2) can be determined by input distance "b" of the specimen(2) and distance "a" of the standard sample(1), and comparison those distances with inputted data.

Next, instead of the standard sample(1), a case where a third sample (hereinafter referred to as control(3)) is used as an indicator sample will be described. The control(3) comprises human serum, for example, prepared as shown below. That is, fresh sera of total cholesterol and total triglyceride values within normal range are collected, to which a mixture of 100 mg of EDTA.2Na.2H$_2$O and 25 g of saccharose is added as a stabilizer in an amount of 2.5 g to 10 cc of serum. Next, the mixture is divided into small items and freeze-dried or frozen at −20. for preservation. The freeze-dried and stored control(3) is dissolved with equal volume of distilled water or purified water prior to use. The frozen control(3) is thawed at room temperature prior to use.

When the thus prepared control(3) is subjected to electrophoresis, a diagram as shown in FIG. 1 is obtained. Then, if the standard sample(1) is not available, by previously determining relative mobility of migration distance of the fraction 105 corresponding to LDL of the control(3) (hereinafter simply referred to marker fraction) and migration distance of LDL fraction of the sample(1), the degree of modification can be determined by conversion as well.

For example, where distance from the application point to the central position of LDL fraction is assumed, as "a" in the standard sample(1), as "b" in the specimen(2), and distance from the application point to the central position of the marker fraction as "c" in the control(3), a relative mobility "$z_1$" of the control (3) to the standard sample(1) is represented by "$z_1=c/a$" (that is, "$a=c/z_1$"). On the other hand, a relative mobility "$z_2$" of the specimen(2) to the standard sample(1) is represented by "$z_2=b/a$". Therefore, "$z_1=b \cdot z_1/c$", if the distance "a" of the standard sample cannot be measured, when the relative mobility "$z_1$" to the control(3) is previously known, the relative mobility "$z_1$" can be determined by measuring distance "c" of the control(3) and distance "b" of the specimen(2). Further, the obtained relative mobility "$z_1$" can be optionally processed as shown the above to determine a degree of modification.

Next, a case where alcohol dehydrogenation enzyme comprising the marker as an indicator sample is used instead of the standard sample(1) or the control(3) will be described. In FIG. 1, a fourth sample (hereinafter also referred to as sample(4)) is a sample prepared by adding a marker comprising a horse-originated alcohol dehydrogenation enzyme to the specimen. Further, a fifth sample (hereinafter also referred to as sample(5)) is a sample prepared by adding a marker comprising a bacteria-originated alcohol dehydrogenation enzyme to the specimen.

For the respective markers (also referred to as indicator samples) comprising horse or bacteria-originated alcohol dehydrogenation enzyme, the alcohol dehydrogenation enzyme is prepared into an ammonium sulfate dispersion and prepared so that when 1 μL of alcohol dehydrogenation enzyme is added to 50 μL of sample, a color development amount is about 80 mg/dL in cholesterol concentration, and mixing ratio of each enzyme and ammonium sulfate is adjusted.

Further, for example, when investigating a degree of modification of cholesterol contained in the lipoprotain, to develop color of the marker (for example, TITAN GEL S CHOLESTEROL commercialized from HELENA LABORATORIES CO., LTD. (Japan)) comprising alcohol dehydrogenation enzyme, 1 μL of ethanol is added as a plate of the alcohol dehydrogenation enzyme to 1 mL of cholesterol measuring reagent. As a result, by ethanol and NAD in the cholesterol measuring reagent and the alcohol dehydrogenation enzyme in the reagent, NAD is converted to NADH$^+$H, further by diaphorase and tetrazolium salt in the alcohol dehydrogenation enzyme, forming formazan same as in the cholesterol measuring reagent, when reacting with cholesterol, which develops a color. Here, the above NADH$^+$H may be detected by fluorescent measurement using fluorescent measuring reagent such as REP Flur Cholesterol Profile-Kit commercialized from HELENA LABORATORIES CORPORATION (U.S.A.).

When the thus prepared marker comprising horse or bacteria-originated alcohol dehydrogenation enzyme is mixed with the specimen and subjected to electrophoresis, an electrophoretic pattern as shown in FIG. 1 is obtained. When a sample(4) comprising the marker and the specimen is used, the marker is separated from the specimen and a marker fraction 106 is obtained which is positioned at the opposite side to LDL fraction 104 contained in the specimen to the application point. This fraction 106 is regarded as the fraction corresponding to LDL fraction of the already described standard sample(1). Further, when the sample(5) is used, the marker fraction 107 generated between VLDL fraction and HDL fraction is regarded as fraction corresponding to LDL of the standard sample(1). In each case, by previously determining the relative mobility of distance "a" of the standard sample(1) with respect to distance "c" from the application point of the sample (4) or (5) to the marker, the degree of modification=of modified LDL in the specimen can be investigated using the same procedure as the case of using the control(3). In the case of using the, sample(4), there is an advantage that quantitative determination of other fractions can be easily performed without adding the marker fraction. The case of using the sample(5) has an advantage that it is not necessary to perform temperature control so strictly during electrophoresis.

Further, a marker comprising horse or bacteria-originated alcohol dehydrogenation enzyme can be added to the control (3) and used.

The above is the gist of a method for separating and assaying lipoprotein according to the present invention. However, the degree of modification in the present invention may be not only a comparison of the standard sample or the indicator sample and the specimen but also a comparison of conspecific samples. For example, when modification of conspecific sample in vitro to an original sample is examined, the original sample is used as a standard sample and inputted a positive integer 1 on item of the relative mobility.

The above-described separation and assay of lipoprotein is method by electrophoresis using agarose plate can be used in a system constructed as shown below.

<Configuration and Operation of System for Separating and Assaying Lipoprotein>

Figure 2:
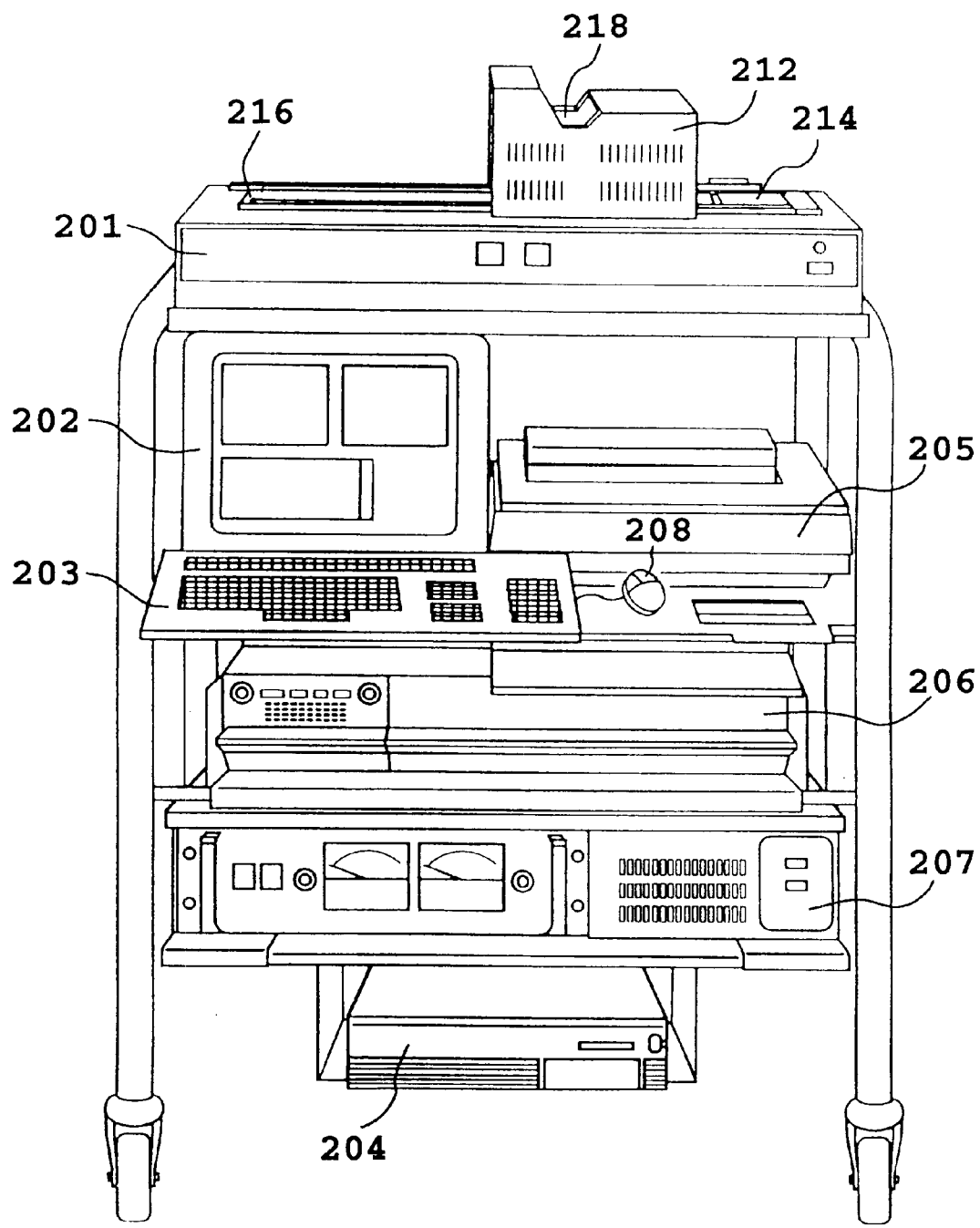
FIG. 2 is a schematic diagram for explaining a system for separating and assaying lipoprotein comprising an electrophoretic apparatus, a densitometer, and a computer, applied to a method for separating and assaying lipoprotein according to the present invention.

FIG. 2 is a diagram showing a construction example of the system for separating and assaying lipoprotein according to the present invention. The system for separating and assaying lipoprotein comprises an automatic electrophoretic apparatus 201 for performing separation of lipoprotein, a densitometer 206 for reading the electrophoretic pattern obtained by the automatic electrophoretic apparatus 201, and a computer main body 204 for controlling operation of the automatic electrophoretic apparatus 201 and the densitometer 206 and processing data from the densitometer 206 according to method for separating and assaying lipoprotein of the present invention and outputting or storing the processing results to the display screen, storage medium, printer or the like.

The automatic electrophoretic apparatus 201 has the same configuration as a commonly used electophoretic apparatus having a sample table 214, an applicator 212, a reagent bottle stand 218, and an electrophoretic chamber 216.

The densitometer 206 is a device for measuring density of each component fractionated by electrophoresis utilizing absorption and reflection of light, which is connected to the computer main body 204 and operation thereof is controlled by the computer.

The computer comprises the computer main body 204, input devices(keyboard 203, mouse 208), a display device (CRT) 202, and an output device(printer) 205.

Reference numeral 207 in the figure indicates a power supply for supplying power to the electrophoretic apparatus 201.

Next, operation of the above-constructed assembly for separating and assying lipoprotein will be described.

First, fractionation of lipoprotein using the automatic electrophoretic apparatus 201 and preparation of electrophoretic pattern of the lipoprotein are performed. Since the ordinary operation of electrophoretic process is well known to a skill in the art except for points specific to the present invention, description will be simplified.

Development of the sample can be performed, as shown in FIG. 1, by a combination of the standard sample(1) with specimen(2), or a combination of specimen(2) with control (3). In the case of the sample(4) or sample(5) containing the marker, development of each sample can be performed in combination with the specimen(2) or alone by mixing with the specimen(2).

In the following, an example of separation and assay of lipoprotein using the system for separating and assaying lipoprotein shown in FIG. 2 will be described.

First, an agarose thin film used for the plate of the electrophoretic apparatus is prepared by solidifying a predetermined amount of agarose solution. At this time, to form the agarose thin film to a desired shape, a plastic thin film provided with set pin holes 102 and 103 (see FIG. 1) and a metal die provided with pins for corresponding to these holes and enabling positioning are used. In the present electrophoretic apparatus, it is formed so that the agarose plate can hold electrophoretic buffer solution. For this purpose, the metal die is thick at the electrode part for holding the buffer solution, and patterned so that a sample hole 101 is formed at a sample application part. The set pin holes 102 and 103 of the plastic thin film are aligned to the above. metal die, pressed with a flat plate from the upper side, then agarose solution is poured into the metal die, and solidified to prepare the agarose thin film. The agarose thin film may be previously prepared and stored, or a commercial product such as REP LIPO 30 PLATE commercialized from HELENA LABORATORIES CO., LTD. (Japan) be used.

Next, in the elecrophoretic chamber 216 of FIG. 2, two set pin holes 102 and 103 (see FIG. 1) of the agarose thin film used in the assay are inserted to set pins (not shown) of the electrophoretic chamber 216 to closely contact with the bottom of the electrophoretic chamber 216. A reagent development rod having magnetic bodies at both ends and an electrode rod are attracted to the electrode as a magnet so as to contact with the agarose thin film (electrophoretic plate), and the door of the electrophoretic chamber is closed. A cholesterol reagent bottle is prepared on the reagent bottle stand 218, and sample is taken on the sample table 214.

After completion of preparation for electrophoresis as described above, electrophoresis is started to prepare an electrophoretic pattern. First, an electrophoresis starting instruction is inputted from the keyboard 203. This sends electrophoresis starting instruction from the computer to the electrophoretic apparatus.

Figure 3:
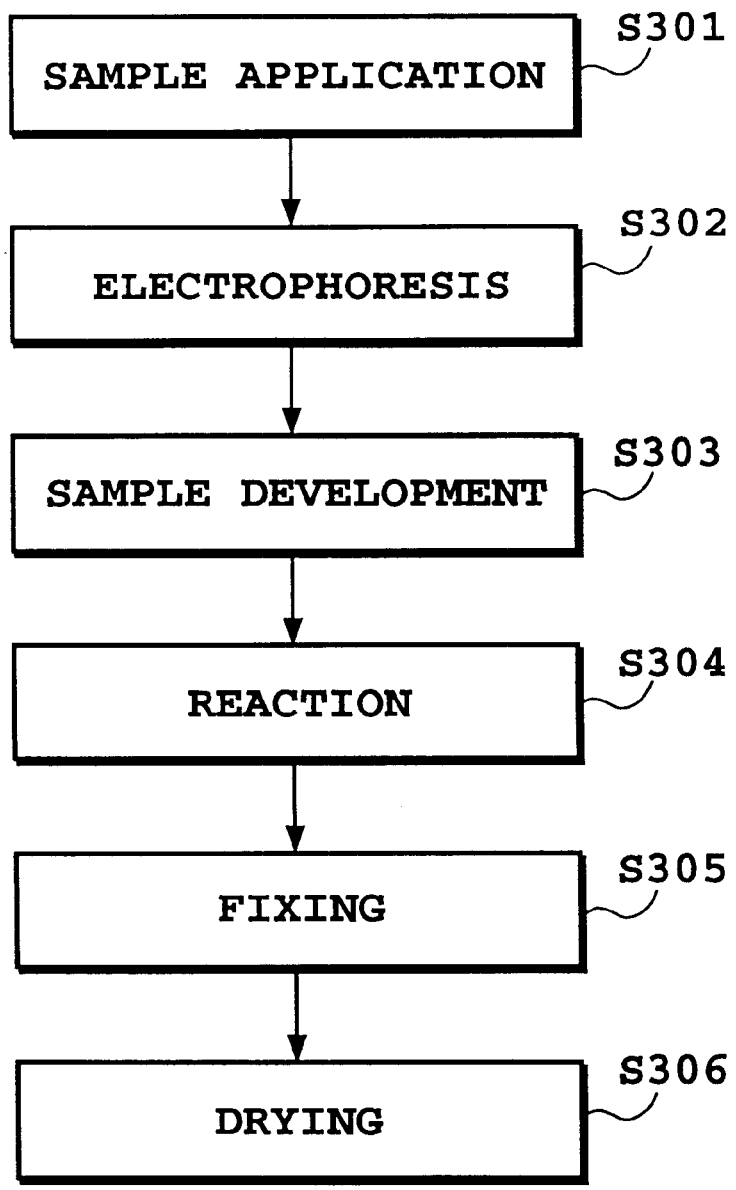
FIG. 3 is a flow chart for explaining an electrophoretic pattern preparation process by electrophoresis applied to a method for separating and assaying lipoprotein according to the present invention.

In the following, preparation procedure of electrophoretic pattern will be described with reference to FIG. 3.

When the electrophoretic apparatus 201 receives the electrophoresis starting instruction from the computer main body 204, the sample on the sample table 214 is injected in a sample groove 101 (S301).

Next, the agarose thin film is applied with an electric voltage to start electrophoresis (S302).

After the passage of a predetermined time and completion of electrophoresis, color development reagent such as cholesterol measuring reagent is developed (S303).

The agarose thin film is impregnated and reacted with the color development reagent to stain the agarose thin film for a predetermined time and at a predetermined temperature (e.g. 30) (S304).

As a color development reagent for detecting cholesterol component, a cholesterol measuring reagent such as TITAN GEL S CHOLESTEROL commercialized from HELENA LABORATORIES CO., LTD. (Japan) can be used. Next, the stained agarose thin film is fixed with 5% acetic acid (S305) and dried (S306).

As a result of such an experiment, for example, an electrophoretic pattern as shown in FIG. 1 (hereinafter referred to as electrophoretic pattern) is obtained.

After the electrophoretic pattern is obtained using the above-described procedure, the concentration and position of each fraction constituting the electrophoretic pattern developed on the agarose thin film are read by the densitometer 206.

The agarose thin film depicted with the electrophoretic pattern is set in position on the densitometer 206(FIG. 2). That is, pins of an electrophoretic pattern feed 522(FIG. 5) are positioned with the agarose thin film set pin holes 102 and 103 (FIG. 1). Setting of scanning condition of the electrophoretic pattern can be carried out on the screen displayed on CRT202 connected to the computer main body 204. An example of such a screen is shown in FIG. 4.

Figure 4:
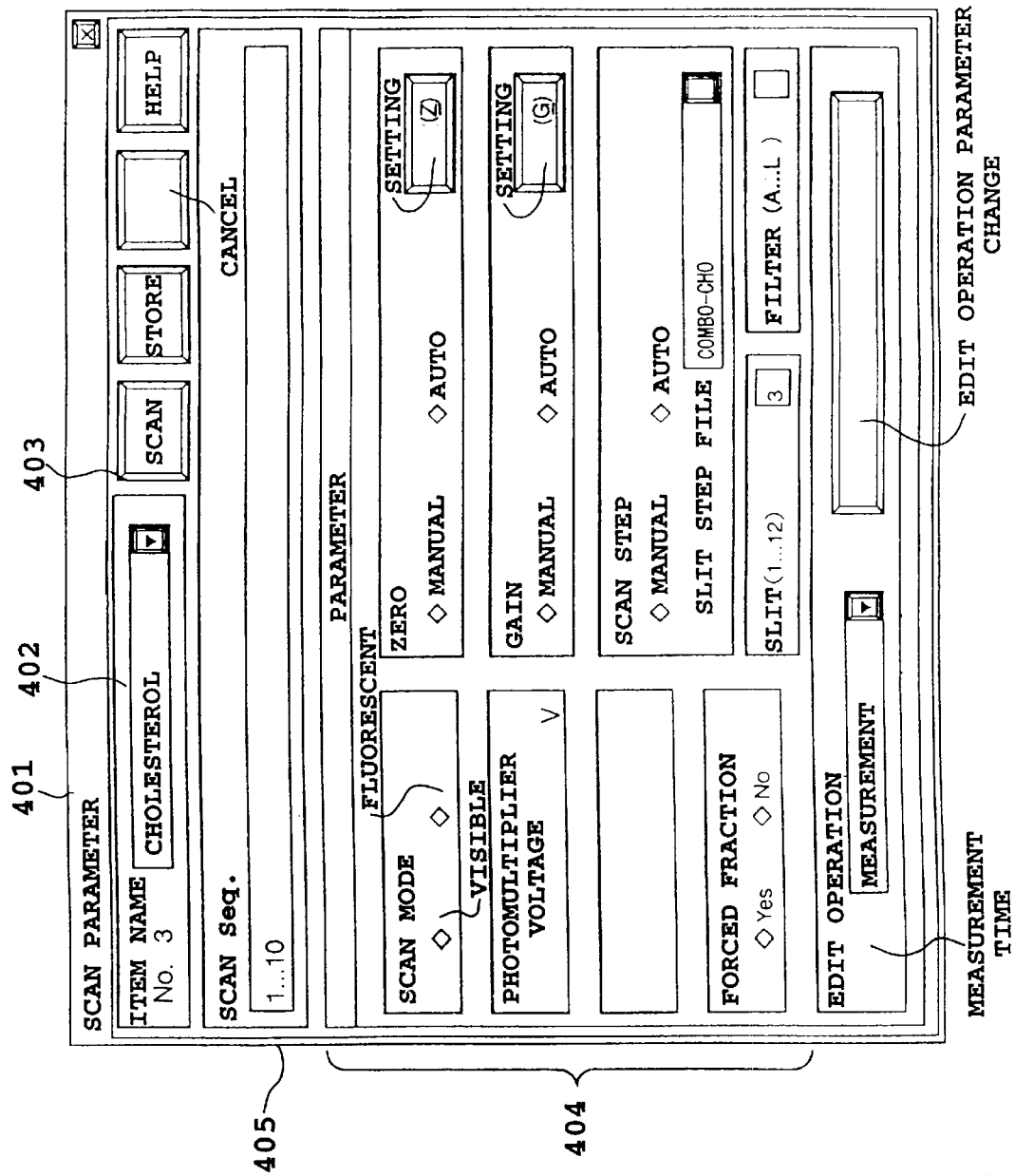
FIG. 4 is a schematic diagram of a measurement condition setting screen displayed on a CRT provided in a system for separating and assaying lipoprotein according to the present invention.

A programming(predetermined application) stored in the computer main body 204 is read to display a scanning condition setting screen (that is, scan parameter setting screen 401) as shown in FIG. 4 on CRT 202. In the scan parameter setting screen 401, name of item to be examined is selected from item name 402, and then scan 403 is instructed to start measurement.

On the shown screen, "Cholesterol" is selected in the item name 402. Setting of further detailed scan condition is performed on parameter setting part 404 at the lower part of the screen, and input of each parameter(condition) is performed utilizing the mouse 208 and the keyboard 203. Alternatively, a previously set default may be used. When it is not necessary to change the default, input of scan sequence(scan Seq.) 405(FIG. 4) is sufficient. In this case, scan button 403 is clicked by the mouse 208 or a predetermined short cut key on the keyboard 203 is pressed.

When scanning of the electrophoretic pattern by the densitometer 206 is started, data of speed of the electrophoretic pattern transported in the densitometer and data of change in light amount transmitted through the electrophoretic pattern detected by the densitometer 206 are inputted to the computer main body 204. Based on these data, relative position and concentration of each fraction constituting the electrophoretic pattern are calculated by the computer main body 204. These processes will be described in detail with reference to FIG. 5.

Figure 5:
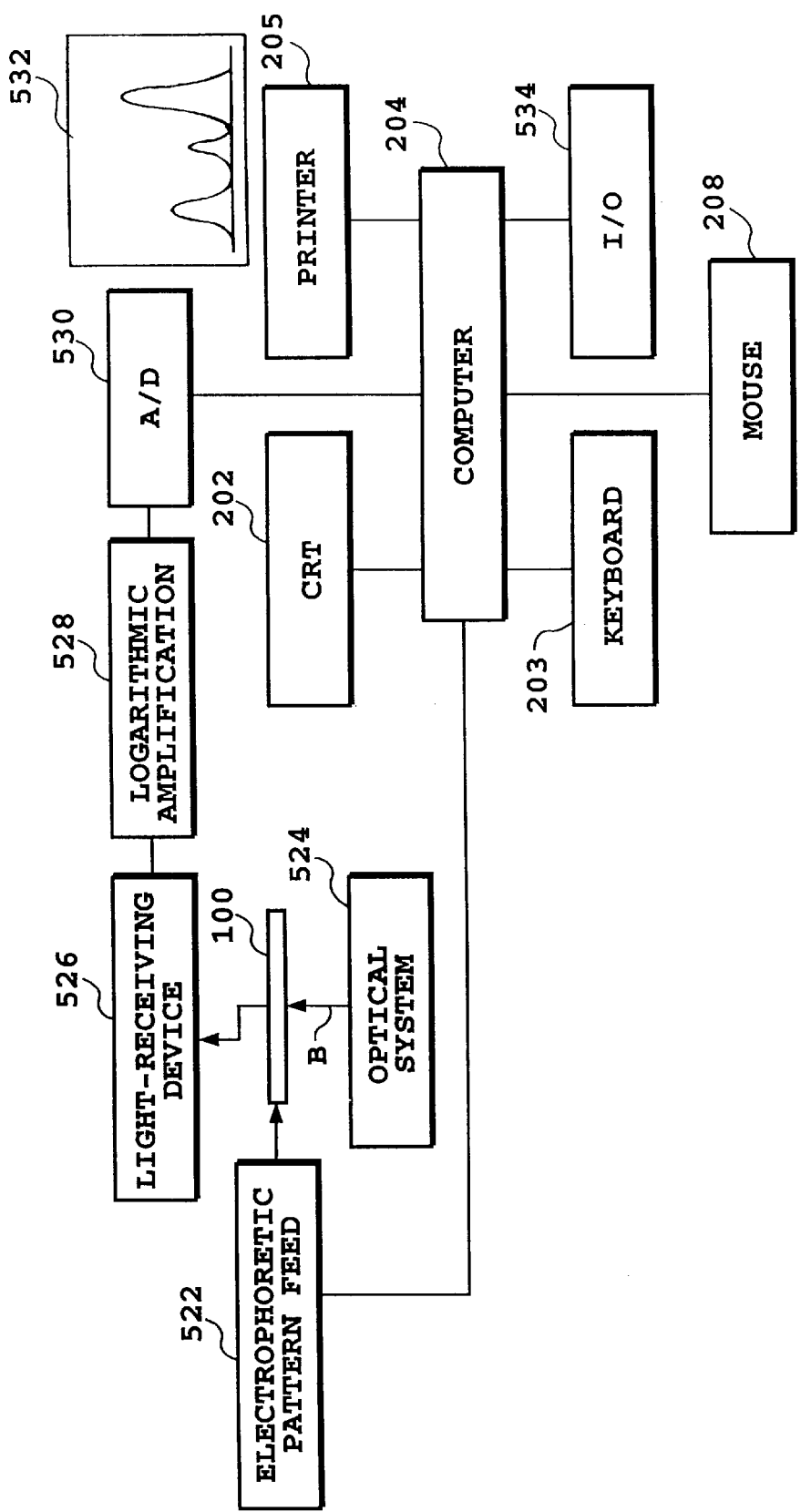
FIG. 5 is a block diagram for explaining configuration of a densitometer and a computer provided in a system for separating and assaying lipoprotein according to the present invention.

FIG. 5 is a block diagram for explaining the configuration of the densitometer and the computer. In the following, for simplicity of explanation, a case where a combination of the specimen(2) and the control(3) is subjected to electrophoresis will be explained.

First, with the measurement preparation completed as above, the scan button 403 is pressed to start measurement.

Beam measurement light (arrow B in the figure) transmitted from an optical system 524 (FIG. 5) passes through a slit (not shown) and through electrophoretic pattern 100. By passing the beam measurement light B through the electrophoretic pattern 100, part of light is absorbed by the electrophoretic pattern 100 to become a change in the beam measurement light B, and the amount of change is caught as an electromotive force by a light receiving device 526. The amount of change caught by the light receiving device 526 is logarithmic-amplified by a logarithmic amplifier 528, converted to a digital value by an A/D converter 530, and stored on a recording medium (for example, hard disk) incorporated in the computer main body 204. By instructing an output of the examination result, a graph 532 plotting an integrated value on the axis of ordinate against the scan direction on the axis of abscissa can be displayed on CRT 202, or outputted to the printer 205. Further, the computer main body 204, based on the integrated value of waveform, converts each fraction to percentage, and concentration of each fraction can be determined from already determined total concentration. Since pins of the electrophoretic pattern feed 522 and electrophoretic pattern set pin holes 102 and 103(FIG. 1) are in line with each other, and the sample application point is determined by the set pin holes 102 and 103, the sample application point is always set in the same position.

Figure 10:
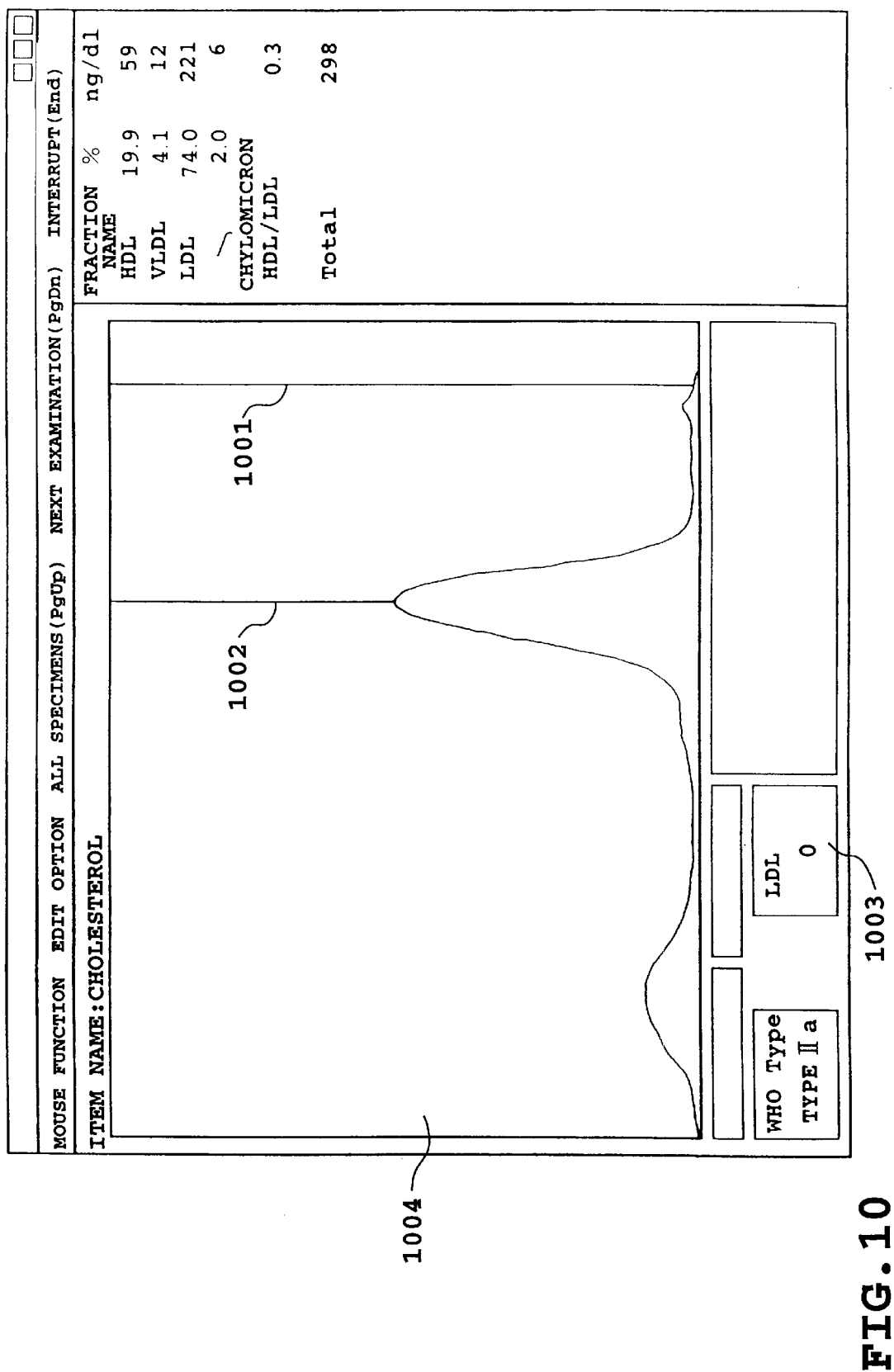
FIG. 10 is a schematic diagram showing a CRT screen displaying graphically and numerically through the computer, displaying results obtained by a densitometer provided in a system for separating and assaying lipoprotein according to the present invention.
Figure 11:
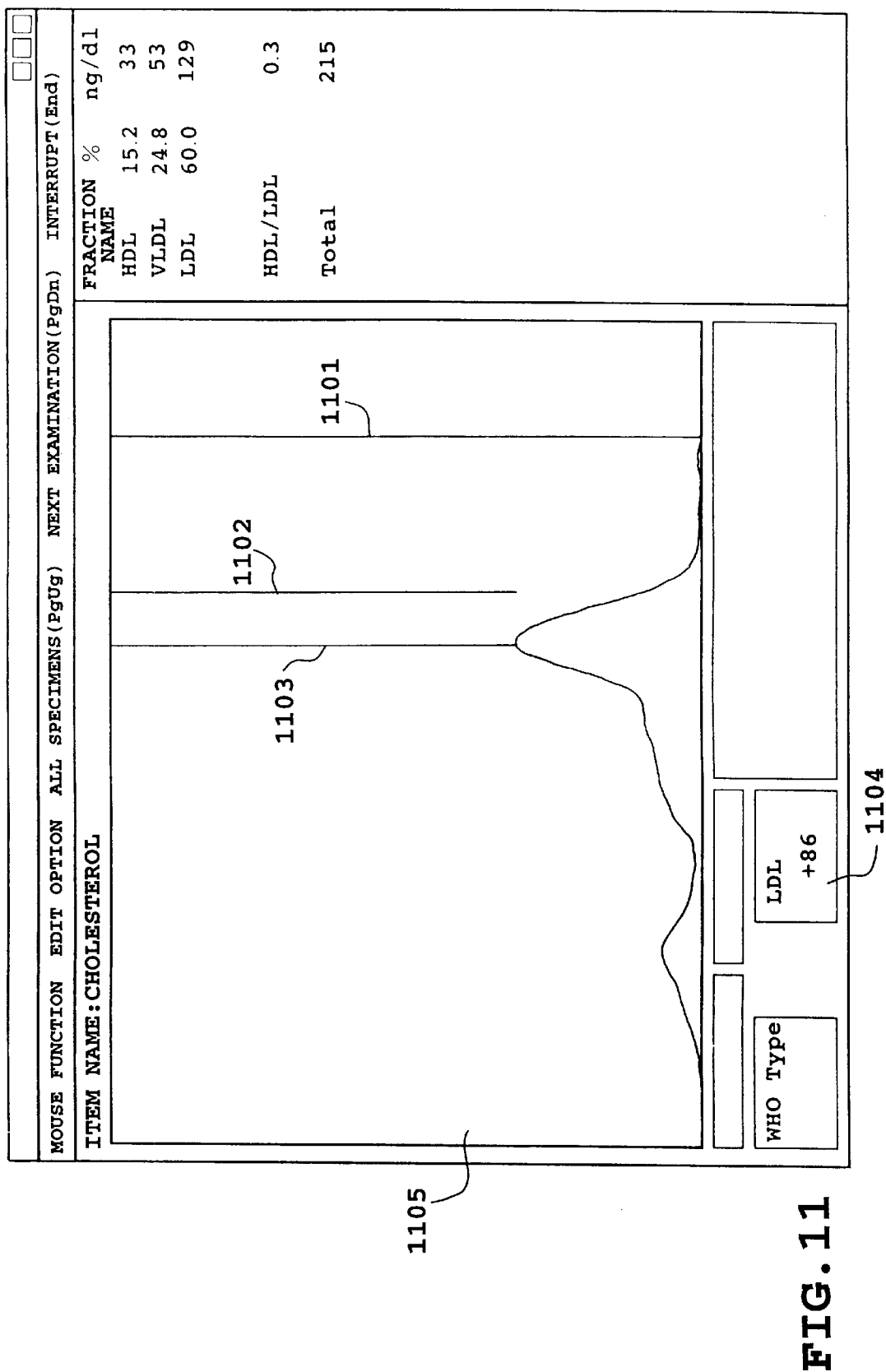
FIG. 11 is a schematic diagram showing a CRT screen displaying graphically and numerically through the computer, displaying results obtained by a densitometer provided in a system for separating and assaying -lipoprotein according to the present invention.
Figure 12:
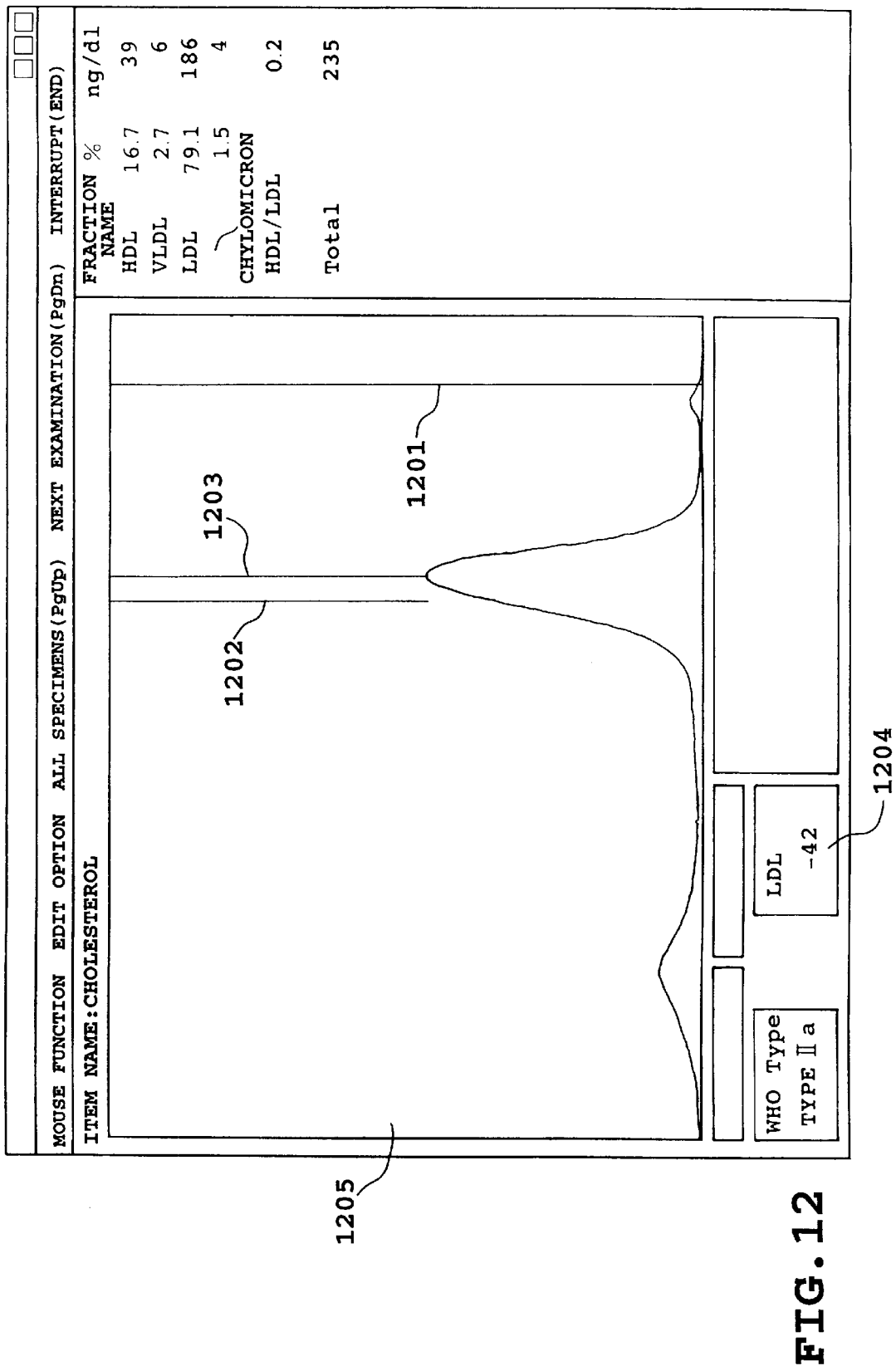
FIG. 12 is a schematic diagram showing a CRT screen displaying graphically and numerically through the computer, displaying results obtained by a densitometer provided in a system for separating and assaying lipoprotein according to the present invention.

Each fraction of lipoprotein containing cholesterol, stained with a cholesterol measuring reagent, shows a specific light absorption spectrum depending on the color development reagent. For example, when cholesterol is detected using a cholesterol measuring reagent such as TITAN GEL S CHOLESTEROL commercialized from HELENA LABORATORIES CO., LTD. (Japan), cholesterol component in lipoprotein reacts with a component in the cholesterol measuring reagent to form formazan. Therefore, the electrophoretic pattern can be scanned at a wavelength of 570 nm corresponding to the absorption spectrum of fornazan. The obtained graph on lipoprotein fraction (cholesterol) is stored on a recording medium such as hard disk. Examples of graph on lipoprotein fraction thus stored on a recording medium are shown in FIGS. 10 to 12 (will be described later).

The computer main body 204 synchronizes with the electrophoretic pattern feed 522 to obtain positional information of the electrophoretic pattern feed. The keyboard 203 is used when inputting an instruction or data to the computer main body 204. The printer 205 is used for preparing an examination result report. An I/O converter 534 is used for communication such as data exchange with terminals of an external computer.

Figure 6:
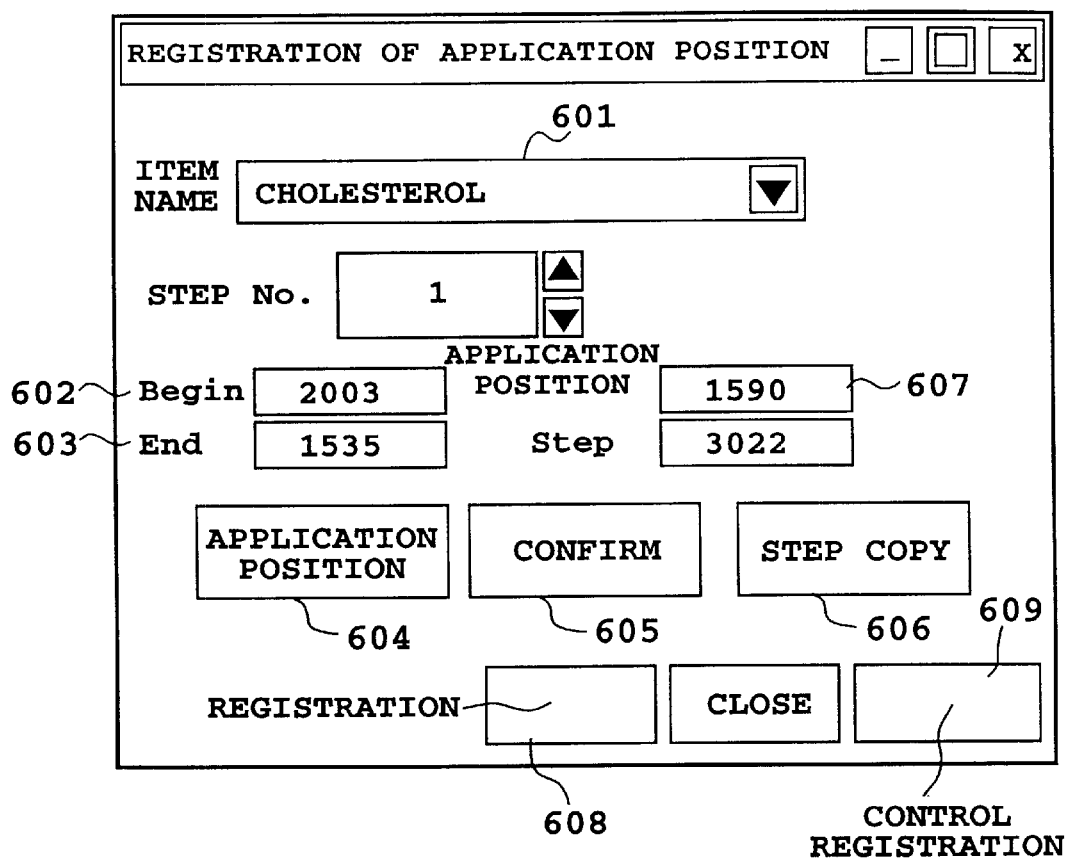
FIG. 6 is a schematic diagram showing a CRT screen for inputting conditions necessary for display setting the application position, as an example of screen displayed on the CRT provided in a system for separating and assaying lipoprotein according to the present invention.

FIGS. 6 and 7 are screens displayed on CRT 202 connected with the computer, for performing input or registration of the application position, control values (data) and the like.

The application position 604(FIG. 6) is clicked with the mouse(FIG. 2) to set the sample application point on the plate for electrophoresis. For example, when performing fractionation measurement of cholesterol as a fraction of lipoprotein, "cholesterol" is instructed on the item name 601. Next, data are inputted to scan start (begin) 602 and scan end (end) 603. When slit beam light of the optical system is coincided with the application point 101 (FIG. 1) of the electrophoretic pattern, and the application position 604 is clicked with the mouse 208 (FIG. 2), data of the application position, for example, numeral "1590", is displayed at the application position 607(FIG. 6). However, the numeral displayed at the application position 607 (here, "1590") must be a numeral lying between numeral "2003" displayed at scan start 602 and numeral "1535" displayed at scan end 603.

When the same setting position is used for the same item, a step copy 606 is clicked with the mouse 208 (FIG. 2) to instruct all step numbers, and the registration 608 (FIG. 6) is clicked to instruct registration. Since, by such operation, data is recorded on the recording medium of the computer, thereafter when fractionation measurement of "cholesterol" is performed, repeated input is unnecessary. When a confirmation button 605 is clicked with the mouse 208, slit beam light moves to position of the application point to confirm whether or not the application position is exactly caught.

When a control registration 609(FIG. 6) is clicked with the mouse 208(FIG. 2), a control value input menu of FIG. 7 is opened.

Next, data (here, "1.125") of relative mobility 701 (FIG. 7) and LDL distance 702(here, "64") are inputted on the screen shown in FIG. 7. Here, the relative mobility 701 is the ratio of the value c of control(3) to the value a of the standard sample(1). Further, the LDL distance 702 shows a distance "c" from the application point of the control (3) to the central position of LDL fraction. The LDL distance 702 is also used for the purpose of correcting delicate differences between various thin films usable as plates for electrophoresis. After the respective values are inputted, when the registration 703 is clicked with the mouse 208(FIG. 2), data is registered on the computer main body 204, and the modification frequency is obtained.

Next, two methods for determining the modification frequency of LDL will be described in detail.

Figure 8:
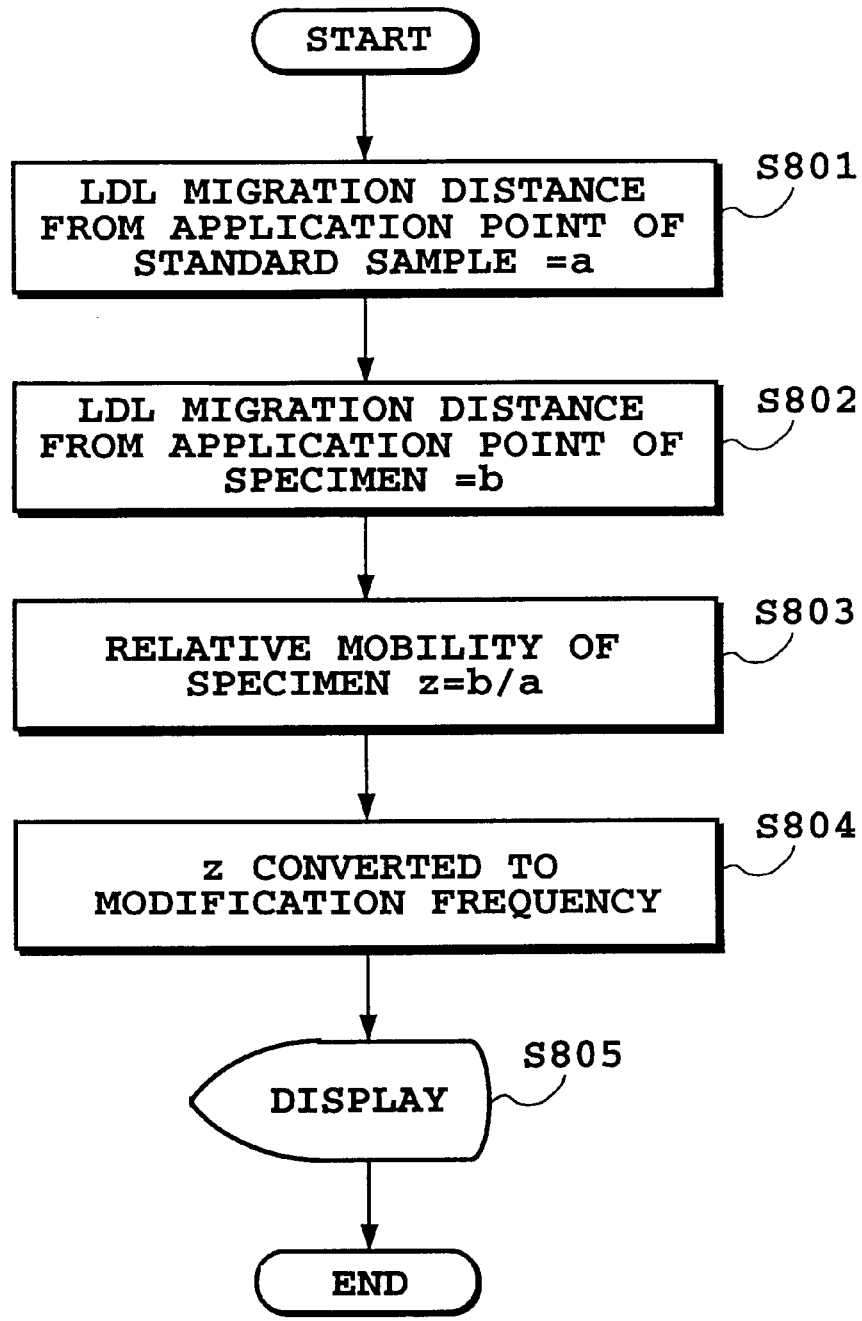
FIG. 8 is a flow chart for explaining a first method for separating and assaying lipoprotein according to the present invention.

A first method will be described with reference to the flow chart shown in FIG. 8. For example, the migration distance "a" from the application point of the standard sample (1) to the central position of LDL fraction is, assumed as a=55 dots (S801), and the migration distance "b" from the application point of the specimen(2) to the central position of LDL fraction as b=70 dots (S802). In this case, relative mobility z is z=b/a=1.273 (S803). The term "dot" used herein, for example, if the measurement range(scanning range) is specified as 256 dots, means that the measurement range is divided by 256.

Since the relative mobility of a specimen(2) of non-modified LDL is "1", the ratio of modification is "1.273−1=0.273". This value "0.273" can be divided by a predetermined value to determine a modification frequency (S804). However, it is necessary to determine how many steps the ratio of modification "0.273" is divided to is appropriate for representing the modification frequency, and the range per division as a predetermined value is incorporated in the program. For example, when the range per division is "0.1", the ratio of modification "0.273" is represented as the modification frequency "2.73" (S805).

Further, by using an appropriate classification symbol such as large, medium, and small, and determining the range of values corresponding to these symbols, previously obtained value (here, "0.273") can be displayed by the symbol of large, medium, or small corresponding to the value. Still further, the obtained value can also be displayed in percentage.

Figure 9:
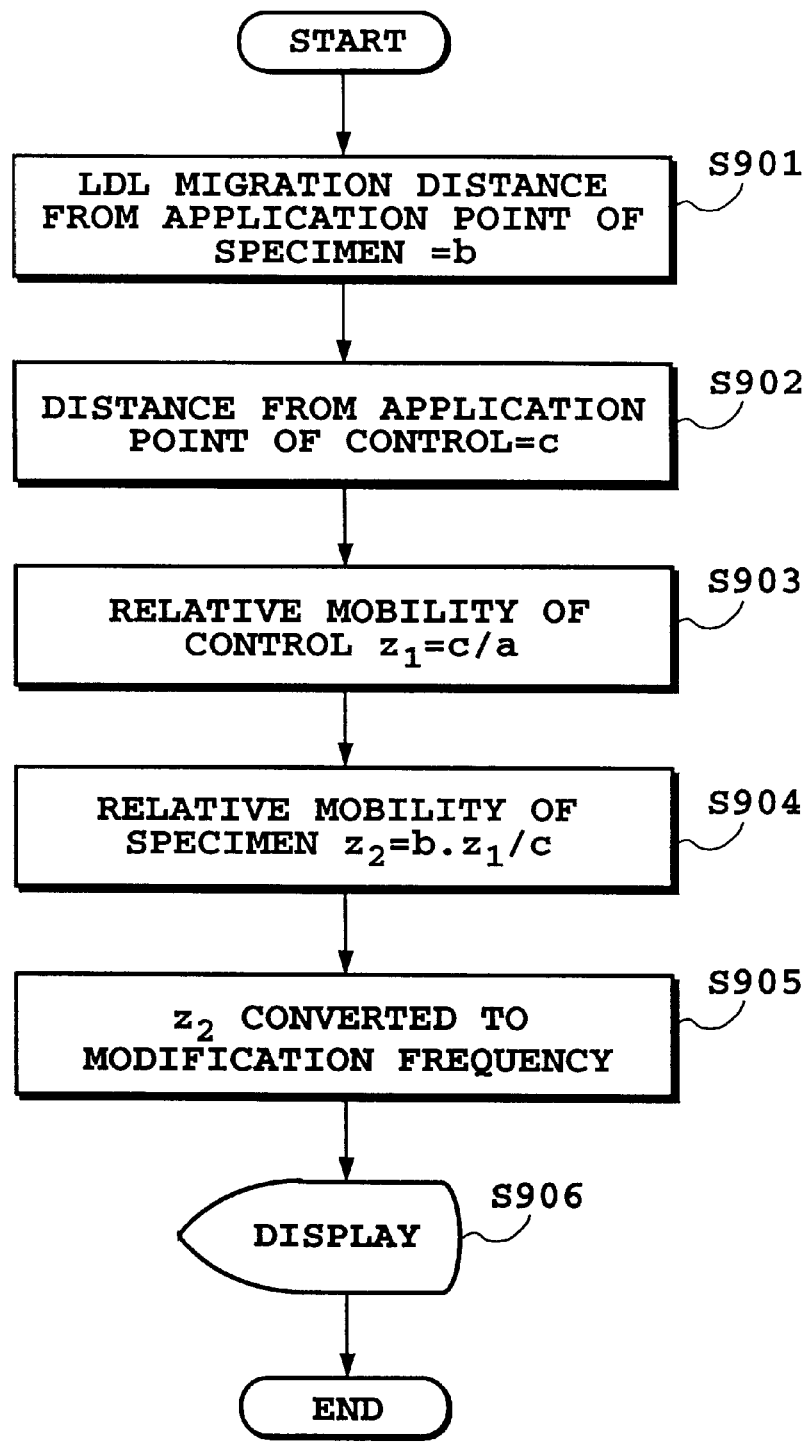
FIG. 9 is a flow chart for explaining a second method for separating and assaying lipoprotein according to the present invention.

Next, a second method will be described with reference to the flow chart shown in FIG. 9. For example, in a case where distance "b" from the application position of the specimen (2) to the central position of LDL fraction is b=70 dots (S901), distance "c" from the application position of the control(3) to the central position of LDL fraction is "c"=60 dots (S902), and relative mobility of the control(3) is "c/a"=

1.125 (S903), the modification frequency of LDL contained in the specimen is determined. Distance "a" from the application position of the standard sample(1) to the central position of LDL fraction is "a"="c/1.125"=53 dots, relative mobility "z" of the specimen(2) and the standard sample(1) is "z"="b/a"=70/53=1.32. Therefore, since relative mobility of specimen(2) not containing modified LDL is "1", the ratio of modification is "1.32−1=0.32" (S904). After that, the ratio of modification of the specimen(2) is converted to the modification frequency using the same procedure as in the above first method (corresponding to S905 in the figure). When the range per division is "0.08", the modification frequency is represented as "4" (S906).

The above description is only exemplification, and any display is possible by specifying appropriate conditions.

FIGS. 10 to 12 are diagrams showing CRT screen showing graphs showing result of assay by the computer of information obtained by the densitometer (cholesterol concentration and positional distribution). In the graph of the figure, the axis of abscissa represents fraction development position and the axis of ordinate represents an optical density or an absorbance. Further, in the part adjacent to the graph on the screen, ratios and concentrations of HDL, VLDL, LDL and the like detected by cholesterol are displayed, and in the lower part thereof, ratio of HDL and LDL is shown.

First, FIG. 10 will be described. This figure shows a case where modified LDL is not contained in the specimen(2) (corresponding to the standard sample(1)). In graph 1004 on the figure, straight line 1001 shows the position of the application point, straight line 1002 shows the central position(at the peak of the curve) of LDL fraction of the standard sample(1) of no modification, and the central position(at the peak of the curve) of LDL fraction of the specimen(2). The modification frequency is displayed at 1003, however, since in FIG. 10, the position of the standard sample(1) and the central position of LDL of the specimen (2) are overlapped, the modification frequency shows zero.

Next, FIG. 11 shows a case where modified LDL is contained in the specimen. In graph 1105 on the figure, straight line 1101 shows the position of the application point, straight line 1102 shows the central position(at the peak of the curve) of LDL fraction of standard sample(1), and straight line 1103 shows the central position (at the peak of the curve) of LDL fraction of the specimen(2). Since the modification frequency 1104 is displayed as "+86", it is understood that LDL is modified.

Further, FIG. 12 shows a case where modified LDL is contained in the specimen(2), and the modification frequency is a negative value. In graph 1205 on the figure, straight line 1201 shows the position of the application point, straight line 1202 shows the central position(at the peak of the curve) of LDL fraction of the standard sample (1), and straight line 1203 shows the central position(at the peak of the curve) of LDL fraction of the specimen(2). Since the central position of standard LDL fraction is at the left side of the central position of LDL fraction of the specimen (2), and distance from the application point to the central position is long, modification 1204 is a negative value as "−42". A negative value of modification frequency shows that electrophoretic speed of LDL of specimen(2) is slower than LDL electrophoretic speed of the standard sample(1), which is useful for the detection of abnormal LDL appearing in hepatic or biliary tract diseases.

When modification frequency is automatically determined using result of separating and assaying lipoprotein by electrophoresis as described above, it is easy to establish plans for diagnosis and dietary treatment or drug treatment according to the diagnostic results.

The graphs displayed on the above screens can be outputted from the printer 205(FIG. 5) by operator instruction.

In the above description, examination of lipoprotein in serum has been described with an eye on the position and concentration of cholesterol contained in the lipoprotein. However, it is needless to say that the present invention is not limited to cholesterol but can be applied to other lipid components or protein components.

Further, in the present specification, cases to serum samples on the plate by agarose electrophoretic process are described. However, the method for separating and assaying lipoprotein according to the present invention can also be applied to samples separated by electrophoresis using various thin films that can be used as plates such as cellulose acetate, agar, and the like. Still further, the method for separating and assaying lipoprotein according to the present invention can be applied not only to electrophoresis using various thin films but also to a case of using capillary electrophoresis. In the case of using a capillary electrophoretic device, it is possible to perform the method for separating and assaying lipoproteins in accordance with the procedures as described above after the steps of subjecting a standard or marker sample to the capillary electrophoresis before or after the electrophoresis of a specimen and then obtaining a degree of relative mobility of the desired lipoprotein from a distance between the application point of each sample and the center point of the LDL fraction or the time that elapsed before the separation is completed. In the present method, furthermore, a marker may be a standard substance to be generally used in the capillary electrophoresis. Thus, it is also possible to perform the method for separating and assaying lipoproteins in accordance with the procedures as described above by subjecting a mixture of such a marker and a specimen to the capillary electrophoresis.

Yet further, as described above, since, in the present invention, from the result of electrophoresis of lipoprotein, modified lipid concerning arteriosclerosis, that is, the degree of modification and the modification frequency of modified LDL can be determined, qualitative anomaly of lipid can be easily and effectively performed. According to the present invention, it becomes possible to provide the method for separating and assaying lipoproteins, the assembly for performing such a method, and the system including such an assembly, which allow the most quantitative and reproducible results with greatly enhanced usability thereof for testing a lot of specimens effectively in clinical examinations or the like. According to the present invention, furthermore, the results of the method for separating and assaying lipoproteins can be used in the follow-up of drug efficacy (e.g., efficacy of an anti-oxidizing agent) to observe a curative effect of the drug on the disease. Therefore, it becomes possible to contribute to the cutting of health expenditures in addition to a simplification of making treatment policies (e.g., prescription of therapeutic agent) to take.

The present invention has been described in detail with respect to various embodiments, and it will now be apparent from the foregoing to those skilled in the art that changes and modifications may be made without departing from the invention in its broader aspects, and it is the intention, therefore, in the appended claims to cover all such changes and modifications as fall within the true spirit of the invention.

What is claimed is:

1. An assembly for separating and assaying lipoprotein to determine a degree of modification of a predetermined component of a lipoprotein in a specimen, using an electrophoretic pattern of a standard sample containing a lipoprotein having the predetermined component and an electrophoretic pattern of the specimen containing a lipoprotein having the predetermined component, or a modification thereof, comprising:

an electrophoretic pattern preparation means for performing electrophoresis of the standard sample and the specimen to fractionate lipoprotein of each sample, then staining said predetermined component in each sample using a reagent for detecting said predetermined component, thereby preparing an electrophoretic pattern for each sample, in which said predetermined component is visualized;

a waveform diagram preparation means for optically scanning said electrophoretic patterns, in which said predetermined component is visualized, and converting each electrophoretic pattern into an optical density waveform, thereby preparing waveform diagrams of said predetermined component; and a means for judging the degree of modification of the predetermined component in the specimen by mathematically processing said electrophoretic patterns;

wherein the means for judging the degree of modification of the predetermined component comprises:

a first means for determining a distance "a" from an application point of the standard sample to a central position of a fraction corresponding to the predetermined component in the standard sample, from the waveform diagram of the predetermined component of the standard sample;

a second means for determining a distance "b" from an application point of the specimen to a central position of a fraction corresponding to the predetermined component in the specimen, from the waveform diagram of the predetermined component of the specimen; and a third means for comparing the distance "a" with the distance "b" to determine a relative mobility "z(=b/a)" of the specimen to the standard sample, wherein the degree of modification of the predetermined component in the specimen is judged on the basis of the relative mobility "z".

2. The assembly for separating and assaying lipoprotein as claimed in claim 1, wherein the degree of modification of the predetermined component is obtained as the ratio of modification "M" by substituting the relative mobility "z(=b/a)" into an equation of:

$$M = b/a - 1 = (b-a)/a. \quad (1)$$

3. The assembly for separating and assaying lipoprotein as claimed in claim 1, wherein the degree of modification of the predetermined component is obtained as a modification frequency "M" by substituting the relative mobility "z(=b/a)" into an equation of:

$$M' = k(b/a - 1) = k(b-a)/a \quad (2)$$

wherein "k" is a constant (k>0).

4. The assembly for separating and assaying lipoprotein as claimed in claim 1, wherein the predetermined component is a low-density lipoprotein.

5. The assembly for separating and assaying lipoprotein as claimed in claim 1, wherein the electrophoresis is carried out by an electrophoretic apparatus using a plate comprising agarose gel as a main ingredient.

6. The assembly of claim 1, wherein the predetermined component is a lipid or a protein.

7. The assembly of claim 6, wherein said lipid is cholesterol and said protein is an apoprotein.

8. An assembly for separating and assaying lipoprotein to determine a degree of modification of a predetermined component of a lipoprotein in a specimen, using an electrophoretic pattern of a standard sample containing a lipoprotein having the predetermined component, an electrophoretic pattern of the specimen containing a lipoprotein having the predetermined component, or a modification thereof, and an electrophoretic pattern of an indicator sample containing a marker component capable of being an indicator of the predetermined component, comprising:

an electrophoretic pattern preparation means for performing electrophoresis of the standard sample and the specimen and the indicator sample to fractionate each sample, then staining said components using reagents for detecting the predetermined component in fractions of the standard sample and the specimen, and the marker component in fractions of the indicator sample, thereby preparing electrophoretic patterns for each sample in which said components are visualized;

a waveform diagram preparation means for optically scanning said visualized electrophoretic patterns and converting each of said electrophoretic patterns into an optical density waveform, thereby preparing waveform diagrams of said predetermined components and said marker component; and a means for judging the degree of modification of the predetermined component in the specimen by mathematically processing said electrophoretic patterns; wherein the means for judging the degree of modification of the predetermined component in the specimen has a first measuring means and a second measuring means, whereby the degree of modification of the predetermined component in the specimen is determined by comparing its mobility to the relative mobility of the indicator sample, wherein the first measuring means comprises:

a first means for determining a distance "a" from an application point of the standard sample to a central position of a fraction corresponding to the predetermined component in the standard sample, from the waveform diagram of the standard sample, a second means for determining a distance "c" from an application point of the indicator sample to a central position of a fraction corresponding to the marker component in the indicator sample, from the waveform diagram of the indicator sample, and a third means for comparing the distance "a" with the distance "c" and determining a relative mobility "$z_1$(=c/a)" of the indicator sample to the standard sample, and the second measuring means comprises:

a fourth means for determining from the waveform diagram of the specimen a distance "b" from an application point of the specimen to a central position of a fraction corresponding to the predetermined component in the specimen, and from the waveform diagram of the indicator sample a distance "c" from an application point of the indicator sample to a central position of a fraction corresponding to the marker component in the indicator sample, and a fifth means for determining a relative mobility "$z_2(=b/a=b\cdot z_1/c)$" of the specimen from the relative mobility "$z_1$" determined by the first measuring means and the distance "b" and the distance "c" determined by the second measuring means.

9. The assembly for separating and assaying lipoprotein as claimed in claim 8, wherein the degree of modification of the predetermined component is obtained as the ratio of modification "M" by substituting the relative mobility "$z_2(=b/a=b\cdot z_1/c)$" into an equation of:

$$M = b\cdot z_1/c - 1 \tag{3}.$$

10. The assembly for separating and assaying lipoprotein as claimed in claim 8, wherein the degree of modification of the predetermined component is obtained as a modification frequency "M'" by substituting the relative mobility "$z_2(=b/a=b\cdot z_1/c)$" into an equation of:

$$M = k(b\cdot z_1/c - 1 \tag{4}$$

wherein "k" is a constant (k>0)).

11. The assembly for separating and assaying lipoprotein as claimed in claim 8, wherein the indicator sample contains an alcohol dehydrogenation enzyme capable of being a marker.

12. The assembly for.separating and assaying lipoprotein as claimed in claim 11, wherein in the second measuring means, the fourth means is a means for simultaneously determining the distance "b" and the distance "c" by subjecting a mixture of the indicator sample and the specimen to electrophoresis.

13. The assembly for separating and assaying lipoprotein as claimed in claim 8, wherein the first predetermined component is low-density lipoprotein.

14. The assembly for separating and assaying lipoprotein as claimed in claim 8, wherein the electrophoresis is carried out by an electrophoretic apparatus using a plate comprising agarose gel as a main ingredient.

15. The assembly of claim 8, wherein the predetermined component is a lipid or a protein.

16. The assembly of claim 15, wherein said lipid is cholesterol and said protein is an apoprotein.

17. The method of claim 8, wherein the indicator sample is serum stored by adding a stabilizer.

18. The method of claim 8, wherein the indicator sample is alcohol dehydrogenase as a marker.

19. A method for separating and assaying lipoprotein to determine a degree of modification of a predetermined component of a lipoprotein in a specimen, using an electrophoretic pattern of a standard sample containing a lipoprotein having the predetermined component and an electrophoretic pattern of the specimen containing a lipoprotein having the predetermined component, or a modification thereof, comprising:

performing electrophoresis of the standard sample and the specimen to fractionate lipoprotein of each sample, then staining said predetermined component in each sample, using a reagent for detecting said predetermined component, thereby preparing an electrophoretic pattern for each sample, in which said predetermined component is visualized;

optically scanning said electrophoretic patterns in which said predetermined component is visualized, and converting each electrophoretic pattern into an optical density waveform, thereby preparing waveform diagrams of said predetermined component; and judging the degree of modification of the predetermined component in the specimen by mathematically processing said electrophoretic patterns;

wherein the step for judging the degree of modification of the predetermined component comprises:

determining a distance "a" from an application point of the standard sample to a central position of a fraction corresponding to the predetermined component in the standard sample, the waveform diagram of the predetermined component of the standard sample;

determining a distance "b" from an application point of the specimen to a central position of a fraction corresponding to the predetermined component in the specimen, from the waveform diagram of the predetermined component of the specimen; and comparing the distance "a" with the distance "b" to determine a relative mobility "$z(=b/a)$" of the specimen to the standard sample, wherein the degree of modification of the predetermined component in the specimen is judged on the basis of the relative mobility "z".

20. The method for separating and assaying lipoprotein as claimed in claim 19, wherein the degree of modification of the predetermined component is obtained as the ratio of modification "M" by substituting the relative mobility "$z(=b/a)$" into an equation of:

$$M = b/a - 1 = (b-a)/a \tag{1}.$$

21. The method for separating and assaying lipoprotein as claimed in claim 19, wherein the degree of modification of the predetermined component is obtained as a modification frequency "M'" by substituting the relative mobility "$z(=b/a)$" into an equation of:

$$M = k(b/a - 1) = k(b-a)/a \tag{2}$$

wherein "k" is a constant (k>0)).

22. The method for separating and assaying lipoprotein as claimed in claim 19, wherein the predetermined component is a low-density lipoprotein.

23. The method for separating and assaying lipoprotein as claimed in claim 19, wherein the electrophoresis is carried out by an electrophoretic apparatus using a plate comprising agarose gel as a main ingredient.

24. The method of claim 19, wherein the predetermined component is a lipid or a protein.

25. The method of claim 24, wherein said lipid is cholesterol and said protein is an apoprotein.

26. A method for separating and assaying lipoprotein to determine a degree of modification of a predetermined component of a lipoprotein in a specimen, using an electrophoretic pattern of a standard sample containing a lipoprotein having the predetermined component, an electrophoretic pattern of the specimen containing a lipoprotein having the predetermined component, or a modification thereof, and an electrophoretic pattern of an indicator sample containing a marker component capable of being an indicator of the predetermined component, comprising:

performing electrophoresis of the standard sample and the specimen and the indicator sample to fractionate each sample, then staining said components using reagents for detecting the predetermined component in fractions of the standard sample and the specimen, and the marker component in fractions of the indicator sample, thereby preparing electrophoretic patterns for each sample in which said components are visualized;

optically scanning said visualized electrophoretic patterns and converting each of said electrophoretic patterns into an optical density waveform, thereby preparing waveform diagrams of said predetermined components and the marker component; and judging the degree of modification of the predetermined component in the specimen by mathematically processing said electrophoretic patterns; wherein the step for judging the degree of modification of the predetermined component has a first measuring step and a second measuring step, whereby the degree of modification of the predetermined component in the specimen is determined by comparing its mobility to the relative mobility of the indicator sample, wherein the first measuring step comprises:

determining a distance "a" from an application point of the standard sample to a central position of a fraction corresponding to the predetermined component in the standard sample, from the waveform diagram of the standard sample, determining a distance "c" from an application point of the indicator sample to a central position of a fraction corresponding to the marker component in the indicator sample, from the waveform diagram of the indicator sample, and comparing the distance "a" with the distance "c" and determining a relative mobility "$z_1(=c/a)$" of the indicator sample to the standard sample, and the second measuring step comprises:

determining from the waveform diagram of the specimen a distance "b" from an application point of the specimen to a central position of a fraction corresponding to the predetermined component in the specimen, determining from the waveform diagram of the indicator sample a distance "c" from an application point of the indicator sample to a central position of a fraction corresponding to the marker component in the indicator sample, and determining a relative mobility "$z_2(=b/a=b \cdot z_1/c)$" of the specimen from the relative mobility "$z_1$" determined by the first measuring step and the distance "b" and the distance "c" determined by the second measuring step.

27. The method for separating and assaying lipoprotein as claimed in claim 26, wherein the degree of modification of the predetermined component is obtained as the ratio of modification "M" by substituting the relative mobility "$z_2 (=b/a=b \cdot z_1/c)$" into an equation of:

$$M = b \cdot z_1/c - 1 \tag{3}$$

28. The method for separating and assaying lipoprotein as claimed in claim 26, wherein the degree of modification of the predetermined component is obtained as a modification frequency "M'" by substituting the relative mobility "$z_2(=b/a=b \cdot z_1/c)$" into an equation of:

$$M = k(b \cdot z_1/c - 1) \tag{4}$$

wherein "k" is a constant (k>0)).

29. The method for separating and assaying lipoprotein as claimed in claim 26, wherein the indicator sample contains an alcohol dehydrogenation enzyme capable of being a marker.

30. The method for separating and assaying lipoprotein as claimed in claim 29, wherein in the second measuring step, the fourth step and the fifth step are simultaneously performed by subjecting a mixture of the indicator sample and the specimen to electrophoresis.

31. The method for separating and assaying lipoprotein as claimed in claim 26, wherein the first predetermined component is a low-density lipoprotein.

32. The method for separating and assaying lipoprotein as claimed in claim 26, wherein the electrophoresis is carried out by an electrophoretic apparatus using a plate comprising agarose gel as a main ingredient.

33. The method of claim 26, wherein the predetermined component is a lipid or a protein.

34. The method of claim 33, wherein said lipid is cholesterol and said protein is an apoprotein.

35. The assembly of claim 26, wherein the indicator sample is serum stored by adding a stabilizer.

36. The assembly of claim 26, wherein the indicator sample is alcohol dehydrogenase as a marker.

* * * * *